United States Patent
Rölle et al.

(10) Patent No.: US 10,241,402 B2
(45) Date of Patent: Mar. 26, 2019

(54) NAPHTHYL ACRYLATES AS WRITING MONOMERS FOR PHOTOPOLYMERS

(71) Applicant: Covestro Deutschland AG, Leverkusen (DE)

(72) Inventors: Thomas Rölle, Leverkusen (DE); Horst Berneth, Leverkusen (DE); Friedrich-Karl Bruder, Krefeld (DE); Dennis Hönel, Zülpich-Wichterich (DE); Serguei Kostromine, Swisttal-Buschhoven (DE); Thomas Fäcke, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/535,086

(22) PCT Filed: Dec. 9, 2015

(86) PCT No.: PCT/EP2015/079152
§ 371 (c)(1),
(2) Date: Jun. 12, 2017

(87) PCT Pub. No.: WO2016/091965
PCT Pub. Date: Jun. 16, 2016

(65) Prior Publication Data
US 2017/0363957 A1    Dec. 21, 2017

(30) Foreign Application Priority Data

Dec. 12, 2014  (EP) .................................... 14197565
Jun. 22, 2015  (EP) .................................... 15173157

(51) Int. Cl.
*G03C 1/73*       (2006.01)
*G03F 7/004*    (2006.01)
(Continued)

(52) U.S. Cl.
CPC ............ *G03F 7/028* (2013.01); *C07C 271/30* (2013.01); *C07C 271/48* (2013.01);
(Continued)

(58) Field of Classification Search
None
See application file for complete search history.

(56) References Cited

U.S. PATENT DOCUMENTS 4,576,998 A * 3/1986 Ellerbe, III .......... C08G 18/671
  525/455
4,965,152 A * 10/1990 Keys ..................... G02B 5/203
  359/15
(Continued)

FOREIGN PATENT DOCUMENTS

EP  0223587 A1  5/1987
EP  2154128 A1  2/2010
(Continued)

OTHER PUBLICATIONS

Lee et al., "Synthesis of novel chiral polymethacrylate bearing urethane and 1,1'binaphthylene moieties and it's chiral recognition ability", Polym. J., vol. 33(5) pp. 411-418 (2001).*
(Continued)

*Primary Examiner* — Martin J Angebranndt
(74) *Attorney, Agent, or Firm* — Drinker Biddle & Reath LLP

(57) ABSTRACT

The invention relates to naphthyl urethane acrylates particularly useful as writing monomers in photopolymer formulations for holographic media. The invention further relates to a photopolymer formulation comprising matrix polymers, writing monomers and photoinitiators, wherein the writing monomers comprise a naphthyl urethane acrylate according to the invention, to a holographic medium comprising matrix polymers, writing monomers and photoinitiators,
(Continued)

wherein the writing monomers comprise a naphthyl urethane acrylate according to the invention, and also to a display comprising a holographic medium according to the invention.

15 Claims, 3 Drawing Sheets

(51) Int. Cl.
| | |
|---|---|
| *G03F 7/028* | (2006.01) |
| *G03H 1/02* | (2006.01) |
| *C07C 271/48* | (2006.01) |
| *C07C 271/30* | (2006.01) |
| *C07C 323/43* | (2006.01) |

(52) U.S. Cl.
CPC ............ *C07C 323/43* (2013.01); *G03C 1/733* (2013.01); *G03F 7/0046* (2013.01); *G03H 2001/022* (2013.01); *G03H 2260/12* (2013.01)

(56) References Cited

U.S. PATENT DOCUMENTS

| | | | | |
|---|---|---|---|---|
| 5,153,237 | A * | 10/1992 | Plotkin | C08F 16/28 522/170 |
| 6,350,826 | B1 * | 2/2002 | Herold | C08F 290/06 525/453 |
| 7,527,837 | B2 * | 5/2009 | Shundo | C09K 19/32 252/299.01 |
| 8,222,314 | B2 * | 7/2012 | Roelle | C07C 323/36 359/3 |
| 9,146,456 | B2 | 9/2015 | Berneth et al. | |
| 2006/0252900 | A1 * | 11/2006 | Bowman | C07C 69/96 526/318 |
| 2009/0068569 | A1 * | 3/2009 | Seta | G03F 7/001 430/2 |
| 2009/0174919 | A1 | 7/2009 | Moss | |
| 2011/0092612 | A1 * | 4/2011 | Miki | C07D 307/91 522/154 |
| 2011/0207086 | A1 * | 8/2011 | Yang | A61K 6/0017 433/215 |
| 2012/0219884 | A1 * | 8/2012 | Weiser | G03F 7/001 430/2 |
| 2012/0219885 | A1 * | 8/2012 | Facke | C07C 271/30 430/2 |
| 2012/0231377 | A1 * | 9/2012 | Weiser | G03F 7/001 430/2 |
| 2012/0321998 | A1 * | 12/2012 | Rolle | G03F 7/001 430/2 |
| 2013/0029081 | A1 * | 1/2013 | Bruder | G11B 7/246 428/64.7 |
| 2013/0252140 | A1 * | 9/2013 | Facke | C07C 323/12 430/2 |
| 2013/0265625 | A1 | 10/2013 | Fäcke et al. | |
| 2016/0353092 | A1 | 12/2016 | Bruder et al. | |
| 2017/0045816 | A1 * | 2/2017 | Facke | G11B 7/24044 |
| 2017/0362165 | A1 * | 12/2017 | Facke | C07C 229/40 |

FOREIGN PATENT DOCUMENTS

| | | | | |
|---|---|---|---|---|
| EP | 2354845 | * | 8/2011 | ............... G03H 1/02 |
| EP | 14155599.5 | | 2/2014 | |
| JP | 2009-185192 | * | 8/2009 | ............ G03F 7/027 |
| JP | 4803331 | B2 * | 10/2011 | ............ C07C 69/54 |
| JP | 2013014533 | A | 1/2013 | |
| WO | WO-2011054818 | A2 | 5/2011 | |
| WO | WO-2012035058 | A1 | 3/2012 | |
| WO | WO-2012062655 | A2 | 5/2012 | |

OTHER PUBLICATIONS

Lee, Y-K., et al., "Synthesis of novel chiral poly(methacrylate)s bearing urethane and cinchona alkaloid moieties in side chain and their chiral recognition abilities", Polymer, 2002, vol. 43, pp. 7539-7547.

English Translation of International Preliminary Report on Patentability with Written Opinion for International Application No. PCT/EP2015/079152, dated Jun. 22, 2017.

International Search Report for PCT/EP2015/079152 dated Feb. 8, 2016.

Written Opinion of the International Searching Authority for PCT/EP2015/079152 dated Feb. 8, 2016.

* cited by examiner

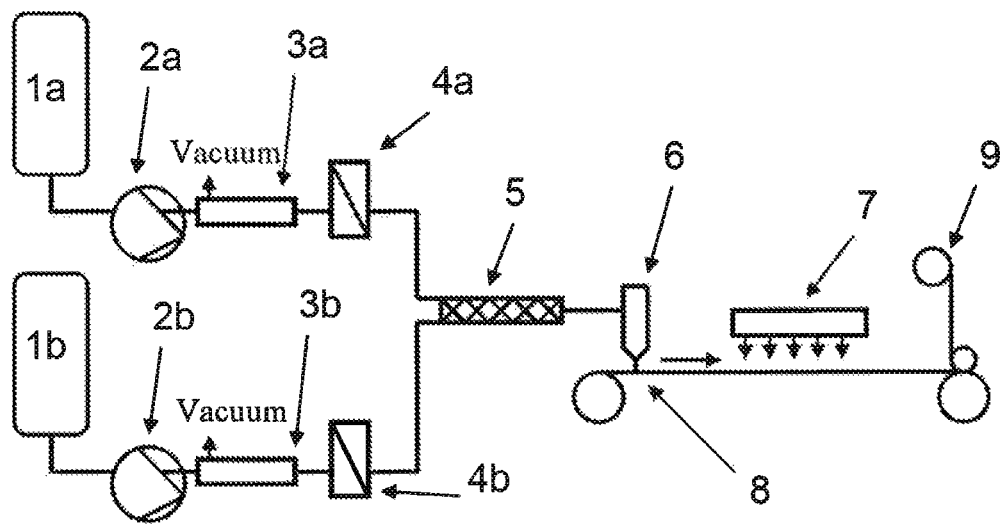
Figure 3: Schematic construction of a continuous film-coating system used (as a roll-to-roll process)

NAPHTHYL ACRYLATES AS WRITING MONOMERS FOR PHOTOPOLYMERS

CROSS-REFERENCE TO RELATED APPLICATIONS

This application is a national stage application (under 35 U.S.C. § 371) of PCT/EP2015/079152, filed Dec. 9, 2015, which claims benefit of European Application Nos. 14197565.6, filed Dec. 12, 2014, and 15173157.7, filed Jun. 22, 2015, all of which are incorporated herein by reference in their entirety.

The invention relates to naphthyl acrylates particularly useful as writing monomers in photopolymer formulations for holographic media. The invention further relates to a photopolymer formulation comprising matrix polymers, writing monomers and photoinitiators, wherein the writing monomers comprise a naphthyl acrylate according to the invention, to a holographic medium comprising matrix polymers, writing monomers and photoinitiators, wherein the writing monomers comprise a naphthyl acrylate according to the invention, and also to a display comprising a holographic medium according to the invention.

BACKGROUND OF THE INVENTION

Photopolymer formulations are known in the prior art. EP 2 154 128 for instance describes a photopolymer formulation containing polyurethane-based matrix polymers, acrylate-based writing monomers, and also photoinitiators. In the cured state, the writing monomers and the photoinitiators form a spatially isotropic distribution embedded in the polyurethane matrix.

For the uses of photopolymer formulations, the crucial role is played by the refractive index modulation Δn produced in the photopolymer by the holographic exposure. In holographic exposure, the interference field of signal light beam and reference light beam (that of two planar waves in the simplest case) is mapped into a refractive index grating by the local photopolymerization of, for example, high-refractive acrylates at loci of high intensity in the interference field. It is the refractive index grating in the photopolymer which is the hologram and which contains all the information in the signal light beam. By illuminating the hologram with only the reference light beam, the signal can then be reconstructed. The strength of the signal thus reconstructed relative to the strength of the incident reference light is called the diffraction efficiency, DE in what follows.

In the simplest case of a hologram resulting from the superposition of two planar waves, the DE is the ratio of the intensity of the light diffracted on reconstruction to the sum total of the intensities of incident reference light and diffracted light. The higher the DE, the greater the efficiency of a hologram with regard to the amount of reference light needed to visualize the signal with a fixed brightness.

High-refractive acrylates are capable of producing refractive index gratings with high amplitude between regions with low refractive index and regions with high refractive index, and hence of enabling holograms with high DE and high Δn in photopolymers. It should be noted here that DE depends on the product of Δn and the photopolymer layer thickness d. The larger the product, the larger the possible DE (for reflection type holograms). The breadth of the angle range at which the hologram is visibly (reconstructed), for example under monochromatic illumination, depends solely on the layer thickness d.

On illumination of the hologram with white light, for example, the breadth of the spectral range which can contribute to the reconstruction of the hologram likewise depends solely on the layer thickness d. The smaller d is, the greater the respective breadths of acceptance. Therefore, if the intention is to produce bright and readily visible holograms, the aim is a high Δn and a low thickness d, so as to maximize DE. This means that, the higher the Δn, the more freedom is achieved to configure the layer thickness d for bright holograms without loss of DE. Therefore, the optimization of Δn is of major importance in the optimization of photopolymer formulations (P. Hariharan, Optical Holography, 2nd Edition, Cambridge University Press, 1996).

BRIEF SUMMARY OF THE INVENTION

The problem addressed by the present invention was that of providing a compound useful as writing monomer in the manufacture of holographic media of high refractive index contrast (Δn). The problem is solved by a compound of formula (I)

Formula (I)

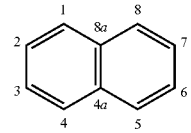

a) which is substituted at at least one of the carbon atoms 4, 5, 6, 7, 8 with a moiety $R_{arcyl}$ of formula (II)

Formula (II)

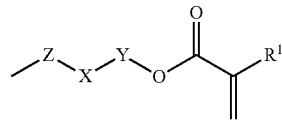

where in said formula (II)
$R^1$ is hydrogen or a $(C_1-C_6)$-alkyl group,
X is a carboxamide (—C(O)N—) or a carboxylic ester (—C(O)O—) or a sulphonamide (—SO$_2$N—) group,
Y is a saturated or unsaturated or linear or branched optionally substituted moiety having 2-10 carbon atoms or a polyether having from one up to five (—CH$_2$—CH$_2$—O—)— or (—C(CH$_3$)H—CH$_2$—O—)— groups or a polyamine having from one to five nitrogen atoms, and
Z is oxygen or sulphur, b) and the compound of formula (I) is at not less than one further carbon atom, 1, 2, 3, 4, 5, 6, 7, 8 substituted with a moiety of formula (III)

Formula (III)

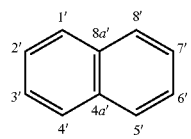

where in said formula (III)
the carbon atoms of the compound of formula (III) are each independently substituted with hydrogen, halogen, a cyano group, a nitro group or an optionally substituted alkyl, alkenyl, alkynyl, aralkyl, aryl or heteroaryl group or an optionally substituted alkoxy or alkylthio group or any substituted carbamoyl group, which also may be linked bridgingly to a moiety of formula (I), or a trifluoromethyl group or a trifluoromethoxy group or a moiety $R_{arcyl'}$ of formula (IV),

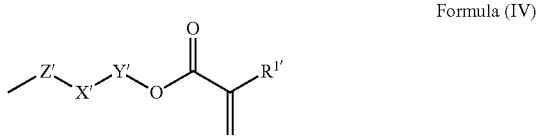

Formula (IV)

where in said formula (IV)
R$^{1'}$ is hydrogen or a (C1-C6)-alkyl group,
X' is a carboxamide (—C(O)N—) or a carboxylic ester (—C(O)O—) or a sulphonamide (—SO$_2$N—) group,
Y' is a saturated or unsaturated or linear or branched optionally substituted moiety having 2-10 carbon atoms or a polyether having from one to five (—CH$_2$—CH$_2$—O—)— or (—C(CH$_3$)H—CH$_2$—O—) groups or a polyamine having from one to five nitrogen atoms, and
Z is oxygen or sulphur,
c) the remaining carbon atoms of the compound of formula (I) are each independently substituted with hydrogen, halogen, a cyano group, a nitro group or an optionally substituted alkyl, alkenyl, alkynyl, aralkyl, aryl or heteroaryl group or an optionally substituted alkoxy or alkylthio group or a trifluoromethyl group or a trifluoromethoxy group.

It was accordingly found that, surprisingly, the compounds of formula (I) are very useful as writing monomer in the manufacture of holographic media of very high refractive index contrast (Δn) and high optical quality.

The compounds of the formula (I) according to the invention are obtainable for example as follows: Oxidative coupling of naphthols may be used to prepare bisnaphthols which are symmetrical or asymmetrical with regard to formula (I) and formula (III) and may optionally be separated preparatively and then may, in a subsequent step of synthesis, be reacted with HO-reactive compounds to form acrylates. It is likewise possible to react commercially available bisnaphthols with HO-reactive compounds to form acrylates. Bridging di- or higher-functional HO-reactive synthons may further also be employed for coupling two bisnaphthols to obtain products which are then further converted into acrylates of formula (I).

DETAILED DESCRIPTION OF THE INVENTION

In a first preferred embodiment of the compound according to the invention, it is substituted with the moiety of formula (III) on the carbon atom in position 5 of formula (I), wherein the moiety of formula (III) may preferably be bonded to the carbon atom in position 5 via the carbon atom in position 8'.

It is likewise preferable when the compound is substituted with the moiety $R_{arcyl}$ of formula (II) on the carbon atom in position 6 of formula (I).

It is also advantageous when the moiety of formula (III) is substituted with the moiety $R_{arcyl'}$ of formula (IV) on the carbon atom in position 7'.

A further preferred embodiment of the invention provides that X is carboxamide in moiety $R_{arcyl}$ and/or X is carboxamide in moiety $R_{arcyl'}$.

In a further advantageous embodiment, R$^1$ is hydrogen or a CH$_3$ moiety in moiety $R_{arcyl}$ and/or R$^{1'}$ is hydrogen or a CH$_3$ moiety in moiety $R_{arcyl'}$.

In a further preferred embodiment, Y may preferably be a —CH$_2$—CH$_2$— moiety in moiety $R_{arcyl}$ and/or Y' may be a —CH$_2$—CH$_2$— moiety in moiety $R_{arcyl'}$.

It is also preferable for Z and/or Z' to each be oxygen.

It is very particularly preferable for Z and/or Z' to each be oxygen and for X and/or X' to each be a carboxamide group.

It is particularly preferably for the compound of the formula (I) according to the invention to be selected from the group of the following substances: 2-[({[2'-({[2-(acryloyloxy)ethyl]carbamoyl}oxy)-1,1'-binaphthyl-2-yl]oxy}carbonyl)amino]ethyl methacrylate, dimethyl 2,2'-bis({[2-(methacryloyloxy)ethyl]carbamoyl}oxy)-1,1'-binaphthyl-3,3'-dicarboxylate, diethyl 2,2'-bis({[2-(methacryloyloxy)ethyl]carbamoyl}oxy)-1,1'-binaphthyl-3,3'-dicarboxylate, 1,1'-binaphthyl-2,2'-diylbis(oxycarbonyliminoethane-2,1-diyl)bisacrylate, 1,1'-binaphthyl-2,2'-diylbis(oxycarbonyliminoethane-2,1-diyl)bis(2-methylacrylate), (6,6'-dicyano-1,1'-binaphthyl-2,2'-diyl)bis(oxycarbonyliminoethane-2,1-diyl) bisacrylate, (6,6'-difluoro-1,1'-binaphthyl-2,2'-diyl)bis(oxycarbonyliminoethane-2,1-diyl) bisacrylate, (6,6'-dichloro-1,1'-binaphthyl-2,2'-diyl)bis(oxycarbonyliminoethane-2,1-diyl) bisacrylate, (6,6'-dibromo-1,1'-binaphthyl-2,2'-diyl)bis(oxycarbonyliminoethane-2,1-diyl) bisacrylate, (6,6'-diiodo-1,1'-binaphthyl-2,2'-diyl)bis(oxycarbonyliminoethane-2,1-diyl) bisacrylate, difluoro-1,1'-binaphthyl-2,2'-diyl)bis(oxycarbonyliminoethane-2,1-diyl) bis(2-methylacrylate), (6,6'-dichloro-1,1'-binaphthyl-2,2'-diyl)bis(oxycarbonyliminoethane-2,1-diyl) bis(2-methylacrylate), (6,6'-dichloro-1,1'-binaphthyl-2,2'-diyl) bis(oxycarbonyliminoethane-2,1-diyl) bis(2-methylacrylate), (6,6'-diiodo-1,1'-binaplithyl-2,2'-diyl)bis(oxycarbonyliminoethane-2,1-diyl) bis(2-methylacrylate), (7,7'-dimethoxy-1,1'-binaphthyl-2,2'-diyl)bis(oxycarbonyliminoethane-2,1-diyl)bisacrylate, (7,7'-diethoxy-1,1'-thyl)bis(oxycarbonyliminoethane-2,1-diyl) bisacrylate, 2-{[({2'-[(hexylcarbamoyl)oxy]-1,1'-binaphthyl-2-yl}oxy)carbonyl]amino}ethyl acrylate, 2-{[({2'-[(butylcarbamoyl)oxy]-1,1'-binaphthyl-2-yl)}oxy)carbonyl]amino}ethyl acrylate, 2-{[({2'-[(hexylcarbamoyl)oxy]-1,1'-binaplithyl-2-yl}oxy)carbonyl]amino}ethyl 2-methylacrylate, 2-{[({2'-[(butylcarbamoyl)oxy]-1,1'-binaphthyl-2-yl}oxy)carbonyl]amino}ethyl 2-methylacrylate, 2-{[({2'-[(hexylcarbamoyl)oxy]-1,1'-binaphthyl-2-yl}oxy)carbonyl]amino}ethyl acrylate, 2-{[({2'-[(hexylcarbamoyl)oxy]-1,1'-binaphthyl-2-yl}oxy)carbonyl]amino}ethyl 2-methylacrylate, 2-{[({2'-[(hexylcarbamoyl)oxy]-1,1'-binaphthyl-2-yl}oxy)carbonyl]amino}ethyl acrylate, 2-{[(2'-[(hexylcarbamoyl)oxy]-1,1'-binaphthyl-2-yl}oxy)carbonyl]amino}ethyl 2-methylacrylate, 2-{[({2'-[(butylcarbamoyl)oxy]-1,1'-binaphthyl-2-yl}oxy)carbonyl]amino}ethyl acrylate, 2-{[({2'-[(butylcarbamoyl)oxy]-1,1'-binaphthyl-2-yl}oxy)carbonyl]amino}ethyl 2-methylacrylate, 2-[({[2'-({[3-(methylsulphanyl)phenyl]carbamoyl}oxy)-1,1'-binaphthyl-2-yl]oxy}carbonyl)amino]ethyl acrylate, 2-[({[2'-({[3-methylsulphanyl)phenyl]carbamoyl}oxy)-1,1'-binaphthyl-2-yl]oxy}carbonyl)amino]ethyl methacrylate, 2-[({[2'-({[2-(methylsulphanyl)phenyl]carbamoyl}oxy)-1,1'-binaphthyl-2-yl]oxy}carbonyl)amino]ethyl acrylate, 2-[({[2'-({[2-(methylsulphanyl)phenyl]carbamoyl}oxy)-1,1'-binaphthyl-2-yl]oxy}carbonyl)amino]ethyl methacrylate, 2-[({[2'-({[4-(methylsulphanyl)phenyl]carbamoyl}oxy)-1, 1'-binaphthyl-2-yl]oxy}carbonyl)amino]ethyl acrylate, 2-[({[2'-({[4-(methylsulphanyl)phenyl]carbamoyl}oxy)-1,1'-binaphthyl-2-yl]oxy}carbonyl)amino]ethyl methacrylate, 2-{[({2'-[(1-naphthylcarbamoyl)oxy]-1,1'-binaphthyl-2-yl}oxy)carbonyl]amino}ethyl acrylate, 2-{[({2'-[(1-naphthylcarbamoyl)oxy]-1,1'-binaphthyl-2-yl}oxy)carbonyl]amino}ethyl methacrylate, hexane-1,6-diylbis(carbamoyloxy-1,1'-binaphthyl-2',2-diyloxycarbonyliminoethane-2,1-diyl) bisacrylate, hexane-1,6-diylbis(carbamoyloxy-1,1'-binaphthyl-2',2-diyloxycarbonyliminoethane-2,1-diyl) bis(2-methylacrylate), (2,2,4-trimethylhexane-1,6-diyl)bis(carbamoyloxy-1,1'-binaphthyl-2',2-diyloxycarbonyliminoethane-2,1-diyl)-bisacrylate, (2,2,4-trimethylhexane-1,6-diyl)bis(carbamoyloxy-1,1'-binaphthyl-2',2-diyloxycarbonyliminoethane-2,1-diyl)-bis(2-methylacrylate), 2-({[(2'-{[(3-{[({[2'-({[2-(acryloyloxy)ethyl]carbamoyl}oxy)-1,1'-binaphthyl-2-yl]oxy}carbonyl)amino]methyl}-3,5,5-trimethylcyclohexyl)carbamoyl]-oxy}-1,1'-binaphthyl-2-yl)oxy]carbonyl}amino)ethyl acrylate, 2-({[(2'-{[(3-{[({[2'-({[2-(methacryloyloxy)ethyl]carbamoyl}oxy)-1,1'-binaphthyl-2-yl]oxy}carbonyl)amino]methyl}-3,5,5-trimethylcyclohexyl)-carbamoyl]oxy}-1,1'-binaphthyl-2-yl)oxy]carbonyl}amino)ethyl methacrylate), (6-fluoro-1,1'-binaphthyl-2,2'-diyl)bis(oxycarbonyliminoethane-2,1-diyl) bisacrylate, (6-fluoro-1,1'-binaphthyl-2,2'-diyl)bis(oxycarbonyliminoethane-2,1-diyl) bis (2-methylacrylate), (6-chloro-1,1'-binaphthyl-2,2'-diyl)bis(oxycarbonyliminoethane-2,1-diyl) bisacrylate, (6-chloro-1,1'-binaphthyl-2,2'-diyl)bis(oxycarbonyliminoethane-2,1-diyl) his (2-methylacrylate), (6-bromo-1,1'-binaphthyl-2,2'-diyl)bis(oxycarbonyliminoethane-2,1-diyl) bisacrylate, (6-bromo-1,1'-binaphthyl-2,2'-diyl)bis(oxycarbonyliminoethane-2,1-diyl) bis (2-methylacrylate), (6-iodo-1,1'-binaphthyl-2,2'-diyl)bis(oxycarbonyliminoethane-2,1-diyl) bisacrylate, (6-iodo-1,1'-binaphthyl-2,2'-diyl)bis(oxycarbonyliminoethane-2,1-diyl) bis (2-methylacrylate), (6-cyano-1,1'-binaphthyl-2,2'-diyl)bis(oxycarbonyliminoethane-2,1-diyl) bisacrylate, (6-cyano-1,1'-binaphthyl-2,2'-diyl)bis(oxycarbonyliminoethane-2,1-diyl) bis(2-methylacrylate), (6-fluoro-6'-cyano-1,1'-binaphthyl-2,2'-diyl)bis(oxycarbonyliminoethane-2,1-diyl) bisacrylate, (6-fluoro-6'-cyano-1,1'-binaphthyl-2,2'-diyl)bis(oxycarbonyliminoethane-2,1-diyl) bis(2-methylacrylate), (6-chloro-6'-cyano-1,1'-binaplithyl-2,2'-diyl)bis(oxycarbonyliminoethane-2,1-diyl) bisacrylate, (6-chloro-6'-cyano-1,1-binaphthyl-2,2'-diyl)bis(oxycarbonyliminoethane-2,1-diyl) bis(2-methylacrylate), (6-bromo-6'-cyano-1,1'-binaphthyl-2,2'-diyl)bis(oxycarbonyliminoethane-2,1-diyl) bisacrylate, (6-bromo-6'-cyano-1,1'-binaphthyl-2,2'-diyl)bis(oxycarbonyliminoethane-2,1-diyl) bis(2-methylacrylate), (6-iodo-6'-cyano-1,1'-binaphthyl-2,2'-diyl)bis(oxycarbonyliminoethane-2,1-diyl) bisacrylate, (6-iodo-6'-cyano-1,1'-binaphthyl-2,2'-diyl)bis(oxycarbonyliminoethane-2,1-diyl) bis(2-methylacrylate).

The invention further provides a photopolymer formulation comprising matrix polymers, writing monomers and photoinitiators, wherein the writing monomers comprise a compound of formula (I) according to the invention.

The matrix polymers of the photopolymer formulation according to the present invention may be particularly in a crosslinked state and more preferably in a three-dimensionally crosslinked state.

It is also advantageous for the matrix polymers to be polyurethanes, in which case the polyurethanes may be obtainable in particular by reacting at least one polyisocyanate component a) with at least one isocyanate-reactive component b).

The polyisocyanate component a) preferably comprises at least one organic compound having at least two NCO groups. These organic compounds may especially be monomeric di- and triisocyanates, polyisocyanates and/or NCO-functional prepolymers. The polyisocyanate component a) may also contain or consist of mixtures of monomeric di- and triisocyanates, polyisocyanates and/or NCO-functional prepolymers.

Monomeric di- and triisocyanates used may be any of the compounds that are well known per se to those skilled in the art, or mixtures thereof. These compounds may have aromatic, araliphatic, aliphatic or cycloaliphatic structures. The monomeric di- and triisocyanates may also comprise minor amounts of monoisocyanates, i.e. organic compounds having one NCO group.

Examples of suitable monomeric di- and triisocyanates are butane 1,4-diisocyanate, pentane 1,5-diisocyanate, hexane 1,6-diisocyanate (hexamethylene diisocyanate, HDI), 2,2,4-trimethylhexamethylene diisocyanate and/or 2,4,4-trimethylhexamethylene diisocyanate (TMDI), isophorone diisocyanate (IPDI), 1,8-diisocyanate-4-(isocyanatomethyl)octane, bis(4,4'-isocyanatocyclohexyl)methane and/or bis(2',4-isocyanatocyclohexyl)methane and/or mixtures thereof having any isomer content, cyclohexane 1,4-diisocyanate, the isomeric bis(isocyanatomethyl)cyclohexanes, 2,4- and/or 2,6-diisocyanato-1-methylcyclohexane (hexahydrotolylene 2,4- and/or 2,6-diisocyanate, $H_6$-TDI), phenylene 1,4-diisocyanate, tolylene 2,4- and/or 2,6-diisocyanate (TDI), naphthylene 1,5-diisocyanate (NDI), diphenylmethane 2,4'- and/or 4,4'-diisocyanate (MDI), 1,3-bis(isocyanatomethyl)benzene (XDI) and/or the analogous 1,4 isomers or any desired mixtures of the aforementioned compounds.

Suitable polyisocyanates are compounds which have urethane, urea, carbodiimide, acylurea, amid, isocyanurate, allophanate, biuret, oxadiazinetrione, uretdione and/or iminooxadiazinedione structures and are obtainable from the aforementioned di- or triisocyanates.

More preferably, the polyisocyanates are oligomerized aliphatic and/or cycloaliphatic di- or triisocyanates, it being possible to use especially the above aliphatic and/or cycloaliphatic di- or triisocyanates.

Very particular preference is given to polyisocyanates having isocyanurate, uretdione and/or iminooxadiazinedione structures, and biurets based on FIDI or mixtures thereof.

Suitable prepolymers contain urethane and/or urea groups, and optionally further structures formed through modification of NCO groups as specified above. Prepolymers of this kind are obtainable, for example, by reaction of the above-mentioned monomeric di- and triisocyanates and/or polyisocyanates a1) with isocyanate-reactive compounds b1).

Isocyanate-reactive compounds b1) used may be alcohols, amino or mercapto compounds, preferably alcohols. These may especially be polyols. Most preferably, isocyanate-reactive compounds b1) used may be polyester polyols, polyether polyols, polycarbonate polyols, poly(meth)acrylate polyols and/or polyurethane polyols.

Suitable polyester polyols are, for example, linear polyester dials or branched polyester polyols, which can be obtained in a known manner by reaction of aliphatic, cycloaliphatic or aromatic di- or polycarboxylic acids or anhydrides thereof with polyhydric alcohols of OH functionality ≥2. Examples of suitable di- or polycarboxylic acids are polybasic carboxylic acids such as succinic acid, adipic acid, suberic acid, sebacic acid, decanedicarboxylic acid, phthalic acid, terephthalic acid, isophthalic acid, tetrahydroplithalic acid or trimellitic acid, and acid anhydrides such as phthalic anhydride, trimellitic anhydride or succinic anhydride, or any desired mixtures thereof. The polyester polyols may also be based on natural raw materials such as castor oil. It is likewise possible that the polyester polyols are based on homo- or copolymers of lactones, which can preferably be obtained by addition of lactones or lactone mixtures, such as butyrolactone, ε-caprolactone and/or methyl-ε-caprolactone onto hydroxy-functional compounds such as polyhydric alcohols of OH functionality ≥2, for example of the hereinbelow mentioned type.

Examples of suitable alcohols are all polyhydric alcohols, for example the $C_2$-$C_{12}$ diols, the isomeric cyclohexanediols, glycerol or any desired mixtures thereof.

Suitable polycarbonate polyols are obtainable in a manner known per se by reaction of organic carbonates or phosgene with diols or diol mixtures.

Suitable organic carbonates are dimethyl, diethyl and diphenyl carbonate.

Suitable diols or mixtures comprise the polyhydric alcohols of OH functionality ≥2 mentioned per se in the context of the polyester segments, preferably butane-1,4-diol, hexane-1,6-diol and/or 3-methylpentanediol. It is also possible to convert polyester polyols to polycarbonate polyols.

Suitable polyether polyols are polyaddition products, optionally of blockwise structure, of cyclic ethers onto OH- or NH-functional starter molecules.

Suitable cyclic ethers are, for example, styrene oxides, ethylene oxide, propylene oxide, tetrahydrofuran, butylene oxide, epichlorohydrin, and any desired mixtures thereof.

Starters used may be the polyhydric alcohols of OH functionality ≥2 mentioned per se in the context of the polyester polyols, and also primary or secondary amines and amino alcohols.

Preferred polyether polyols are those of the aforementioned type based exclusively on propylene oxide, or random or block copolymers based on propylene oxide with further 1-alkylene oxides. Particular preference is given to propylene oxide homopolymers and random or block copolymers containing oxyethylene, oxypropylene and/or oxybutylene units, where the proportion of the oxypropylene units based on the total amount of all the oxyethylene, oxypropylene and oxybutylene units amounts to at least 20% by weight, preferably at least 45% by weight. Oxypropylene and oxybutylene here encompasses all the respective linear and branched $C_3$ and $C_4$ isomers.

Additionally suitable as constituents of the polyol component 131), as polyfunctional, isocyanate-reactive compounds, are also low molecular weight (i.e. with molecular weights ≤500 g/mol), short-chain (i.e. containing 2 to 20 carbon atoms), aliphatic, araliphatic or cycloaliphatic di-, tri- or polyfunctional alcohols.

These may, for example, in addition to the abovementioned compounds, be neopentyl glycol, 2-ethyl-2-butylpropanediol, trimethylpentanediol, positionally isomeric diethyloctanediols, cyclohexanediol, 1,4-cyclohexanedimethanol, 1,6-hexanediol, 1,2- and 1,4-cyclohexanediol, hydrogenated bisphenol A, 2,2-bis(4-hydroxycyclohexyl)propane or 2,2-dimethyl-3-hydroxypropionic acid, 2,2-dimethyl-3-hydroxypropyl ester. Examples of suitable triols are trimethylolethane, trimethylolpropane or glycerol. Suitable higher-functionality alcohols are di(trimethylolpropane), pentaerythritol, dipentaerythritol or sorbitol.

It is especially preferable when the polyol component is a difunctional polyether, polyester, or a polyether-polyester block copolyester or a polyether-polyester block copolymer having primary OH functions.

It is likewise possible to use amines as isocyanate-reactive compounds b1). Examples of suitable amines are ethylenediamine, propylenediamine, diaminocyclohexane, 4,4'-dicyclohexylmethanediamine, isophoronediamine (IPDA), difunctional polyamines, for example the Jeffamines®, amine-terminated polymers, especially having number-average molar masses ≤10 000 g/mol. Mixtures of the aforementioned amines can likewise be used.

It is likewise possible to use amino alcohols as isocyanate-reactive compounds b1). Examples of suitable amino alcohols are the isomeric aminoethanols, the isomeric aminopropanols, the isomeric aminobutanols and the isomeric aminohexanols, or any desired mixtures thereof.

All the aforementioned isocyanate-reactive compounds b1) can be mixed with one another as desired.

It is also preferable when the isocyanate-reactive compounds b1) have a number-average molar mass of ≥200 and ≤10 000 g/mol, further preferably ≥500 and ≤8000 g/mol and most preferably ≥800 and ≤5000 g/mol. The OH functionality of the polyols is preferably 1.5 to 6.0, more preferably 1.8 to 4.0.

The prepolymers of the polyisocyanate component a) may especially have a residual content of free monomeric di- and triisocyanates of <1% by weight, more preferably <0.5% by weight and most preferably <0.3% by weight.

It is optionally also possible that the polyisocyanate component a) contains, entirely or in part, organic compound whose NCO groups have been fully or partly reacted with blocking agents known from coating technology. Example of blocking agents are alcohols, lactams, oximes, malonic esters, pyrazoles, and amines, for example butanone oxime, diisopropylamine, diethyl malonate, ethyl acetoacetate, 3,5-dimethylpyrazole, ε-caprolactam, or mixtures thereof.

It is especially preferable when the polyisocyanate component a) comprises compounds having aliphatically bonded NCO groups, aliphatically bonded NCO groups being understood to mean those groups that are bonded to a primary carbon atom. The isocyanate-reactive component b) preferably comprises at least one organic compound having an average of at least 1.5 and preferably 2 to 3 isocyanate-reactive groups. In the context of the present invention, isocyanate-reactive groups are regarded as being preferably hydroxyl, amino or mercapto groups.

The isocyanate-reactive component may especially comprise compounds having a numerical average of at least 1.5 and preferably 2 to 3 isocyanate-reactive groups.

Suitable polyfunctional isocyanate-reactive compounds of component b) are for example the above-described compounds b1).

A further preferred embodiment provides that the writing monomers comprise a mono- and/or a multi-functional (meth)acrylate writing monotners. It is very particularly preferable for the writing monomers to further comprise at least one mono- and/or a multi-functional urethane (meth)acrylate.

Suitable acrylate writing monomers are especially compounds of the general formula (II)

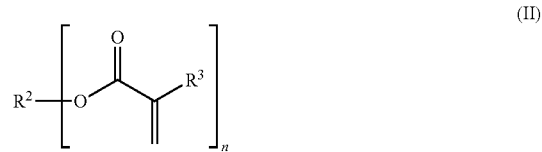

(II)

in which n≥1 and n≤4 and $R^2$ is a linear, branched, cyclic or heterocyclic organic moiety which is unsubstituted or else optionally substituted by heteroatoms and/or $R^3$ is hydrogen or a linear, branched, cyclic or heterocyclic organic moiety which is unsubstituted or else optionally substituted by heteroatoms. More preferably, $R^3$ is hydrogen or methyl and/or $R^2$ is a linear, branched, cyclic or heterocyclic organic moiety which is unsubstituted or else optionally substituted with heteroatoms.

Acrylates and methacrylates refer, respectively, to esters of acrylic acid and methacrylic acid. Examples of acrylates and methacrylates usable with preference are phenyl acrylate, phenyl methacrylate, phenoxyethyl acrylate, phenoxyethyl methacrylate, phenoxyethoxyethyl acrylate, phenoxyethoxyethyl methacrylate, phenylthioethyl acrylate, phenylthioethyl methacrylate, 2-naphthyl acrylate, 2-naphthyl methacrylate, 1,4-bis(2-thionaphthyl)-2-butyl acrylate, 1,4-bis(2-thionaphthyl)-2-butyl methacrylate, bisphenol A diacrylate, bisphenol A ditnethacrylate, and the ethoxylated analogue compounds thereof, N-carbazolyl acrylates.

Urethane acrylates are understood to mean compounds having at least one acrylic ester group and at least one urethane bond. Compounds of this kind can be obtained, for example, by reacting a hydroxy-functional acrylate or methacrylate with an isocyanate-functional compound.

Examples of isocyanate-functional compounds usable for this purpose are monoisocyanates, and the monomeric diisocyanates, triisocyanates and/or polyisocyanates mentioned under a). Examples of suitable monoisocyanates are phenyl isocyanate, the isomeric methylthiophenyl isocyanates. Di-, tri- or polyisocyanates have been mentioned above, and also triphenylmethane 4,4',4"-triisocyanate and tris(p-isocyanatophenyl) thiophosphate or derivatives thereof with urethane, urea, carbodiimide, acylurea, isocyanurate, allophanate, biuret, oxadiazinetrione, uretdione, iminooxadiazinedione structure and mixtures thereof. Preference is given to aromatic di-, tri- or polyisocyanates.

Useful hydroxy-functional acrylates or methacrylates for the preparation of urethane acrylates include, for example, compounds such as 2-hydroxyethyl (meth)acrylate, polyethylene oxide mono(meth)acrylates, polypropylene oxide mono(meth)acrylates, polyalkylene oxide mono(meth)acrylates, poly(ε-caprolactone) mono(meth)acrylates, for example Tone® M100 (Dow, Schwalhach, Del.), 2-hydroxypropyl (meth)acrylate, 4-hydroxybutyl (meth)acrylate, 3-hydroxy-2,2-dimethylpropyl (meth)acrylate, hydroxypropyl (meth)acrylate, 2-hydroxy-3-phenoxypropyl acrylate, the hydroxy-functional mono-, di- or tetraacrylates of polyhydric alcohols such as trimethylolpropane, glycerol, pentaerythritol, dipentaerythritol, ethoxylated, propoxylated or alkoxylated trimethylolpropane, glycerol, pentaerythritol, dipentaerythritol or the technical mixtures thereof. Preference is given to 2-hydroxyethyl acrylate, hydroxypropyl acrylate, 4-hydroxybutyl acrylate and poly(ε-caprolactone) mono(meth)acrylate.

It is likewise possible to use the fundamentally known hydroxyl-containing epoxy (meth)acrylates having OH contents of 20 to 300 mg KOH/g or hydroxyl-containing polyurethane (meth)acrylates having OH contents of 20 to 300 mg KOH/g or acrylated polyacrylates having OH contents of 20 to 300 mg KOH/g and mixtures thereof, and mixtures with hydroxyl-containing unsaturated polyesters and mixtures with polyester (meth)acrylates or mixtures of hydroxyl-containing unsaturated polyesters with polyester (meth)acrylates.

Preference is given especially to urethane acrylates obtainable from the reaction of tris(p-isocyanatophenyl) thiophosphate and/or m-methylthiophenyl isocyanate with alcohol-functional acrylates such as hydroxyethyl (meth)acrylate, hydroxypropyl (meth)acrylate and/or hydroxybutyl (meth)acrylate.

It is likewise possible that the writing monomer comprises further unsaturated compounds such as α,β-unsaturated carboxylic acid derivatives, for example maleates, fumarates, maleimides, acrylamides, and also vinyl ethers, propenyl ethers, allyl ethers and compounds containing dicyclopentadienyl units, and also olefinically unsaturated compounds, for example styrene, α-methylstyrene, vinyltoluene and/or olefins.

Photoinitiators suitable for the purposes of the present invention are compounds activatable typically by means of actinic radiation, which can trigger polymerization of the writing monomers. In the case of the photoinitiators, a distinction can be made between unimolecular (type I) and bimolecular (type II) initiators. In addition, they are distinguished by their chemical nature as photoinitiators for free-radical, anionic, cationic or mixed types of polymerization.

Type I photoinitiators (Norrish type I) for free-radical photopolymerization form free radicals on irradiation through unimolecular bond scission. Examples of type I photoinitiators are triazines, oximes, benzoin ethers, benzil ketals, bisimidazoles, aroylphosphine oxides, sulphonium salts and iodonium salts.

Type II photoinitiators (Norrish type II) for free-radical polymerization consist of a dye as sensitizer and a coinitiator, and undergo a bimolecular reaction on irradiation with light attuned to the dye. First of all, the dye absorbs a photon and transfers energy from an excited state to the coinitiator. The latter releases the polymerization-triggering free radicals through electron or proton transfer or direct hydrogen abstraction.

In the context of this invention, preference is given to using type II photoinitiators.

The dye and the coinitiator of the type II photoinitiators may either be directly mixed conjointly with the further components of the photopolymer or alternatively be singly premixed with individual components. Especially when the photopolymer is to contain polyurethane matrix polymers, the dye may be premixed with the isocyanate-reactive component and the coinitiator with the isocyanate component. It is similarly also possible, however, to premix the coinitiator with the isocyanate-reactive component and the dye with the isocyanate component.

Photoinitiator systems of this kind are described in principle in EP 0 223 587 A and consist preferably of a mixture of one or more dyes with ammonium alkylarylborate(s).

Suitable dyes which, together with an ammonium alkylarylborate, form a type II photoinitiator are the cationic dyes described in WO 2012062655, in combination with the anions likewise described therein.

Cationic dyes are preferably understood to mean those from the following classes: acridine dyes, xanthene dyes, thioxanthene dyes, phenazine dyes, phenoxazine dyes, phenothiazine dyes, tri(het)arylmethane dyes—especially diamino- and triamino(het)arylmethane dyes, mono-, di-, tri- and pentamethinecyanine dyes, hemicyanine dyes, externally cationic merocyanine dyes, externally cationic neutrocyanine dyes, zeromethine dyes—especially naphtholactam dyes, streptocyanine dyes. Dyes of this kind are described, for example, in H. Berneth in Ullmann's Encyclopedia of Industrial Chemistry, Azine Dyes, Wiley-VCH Verlag, 2008, H. Berneth in Ullmann's Encyclopedia of Industrial Chemistry, Methine Dyes and Pigments, Wiley-VCH Verlag, 2008, T. Gessner, U. Mayer in Ullmann's Encyclopedia of Industrial Chemistry, Triarylmethane and Diarylinethane Dyes, Wiley-VCH Verlag, 2000.

Particular preference is given to phenazine dyes, phenoxazine dyes, phenothiazine dyes, tri(het)arylmethane dyes—especially diamino- and triamino(het)arylmethane dyes, mono-, di-, tri- and pentamethinecyanine dyes, hemicyanine dyes, zerotnethine dyes—especially naphtholactam dyes, streptocyanine dyes.

Examples of cationic dyes are Astrazon Orange G, Basic Blue 3, Basic Orange 22, Basic Red 13, Basic Violet 7, Methylene Blue, New Methylene Blue, Azure A, 2,4-diphenyl-6-(4-methoxyphenyl)pyrylium, Safranin O, Astraphloxin, Brilliant Green, Crystal Violet, Ethyl Violet and thionine.

Preferred anions are especially $C_8$- to $C_{25}$-alkanesulphonate, preferably $C_{13}$- to $C_{25}$-alkanesulphonate, $C_3$- to $C_{18}$-perfluoroalkanesulphonate, $C_4$- to $C_{18}$-perfluoroalkanesulphonate bearing at least 3 hydrogen atoms in the alkyl chain, $C_9$- to $C_{25}$-alkanoate, $C_9$- to $C_{25}$-alkenoate, $C_8$- to $C_{25}$-alkylsulphate, preferably $C_{13}$- to $C_{25}$-alkylsulphate, $C_8$- to $C_{25}$-alkenylsulphate, preferably $C_{13}$- to $C_{25}$-alkenylsulphate, $C_3$ to $C_{18}$-perfluoroalkylsulphate, $C_4$- to $C_{18}$-perfluoroalkylsulphate bearing at least 3 hydrogen atoms in the alkyl chain, polyether sulphates based on at least 4 equivalents of ethylene oxide and/or 4 equivalents of propylene oxide, bis($C_4$- to $C_{25}$-alkyl, $C_5$- to $C_7$-cycloalkyl, $C_3$- to $C_8$-alkenyl or $C_7$- to $C_{11}$-aralkyl)sulphosuccinate, bis-$C_2$- to $C_{19}$-alkylsulphosuccinate substituted by at least 8 fluorine atoms, $C_8$- to $C_{25}$-alkylsulphoacetates, benzenesulphonate substituted by at least one radical from the group of halogen, $C_4$- to $C_{25}$-alkyl, perfluoro-$C_1$- to $C_8$-alkyl and/or $C_1$- to $C_{12}$-alkoxycarbonyl, naphthalene- or biphenylsulphonate optionally substituted by nitro, cyano, hydroxyl, $C_1$- to $C_{25}$-alkyl, $C_1$- to $C_{12}$-alkoxy, amino, $C_1$- to $C_{12}$-alkoxycarbonyl or chlorine, benzene-, naphthalene- or biphenyldisuiphonate optionally substituted by nitro, cyano, hydroxyl, $C_1$- to $C_{25}$-alkyl, $C_1$- to $C_{12}$-alkoxy, $C_1$- to $C_{12}$-alkoxycarbonyl or chlorine, benzoate substituted by dinitro, $C_6$- to $C_{25}$-alkyl, $C_4$- to $C_{12}$-alkoxycarbonyl, benzoyl, chlorobenzoyl or tolyl, the anion of naphthalenedicarboxylic acid, diphenyl ether disulphonate, sulphonated or sulphated, optionally at least monounsaturated $C_8$ to $C_{25}$ fatty acid esters of aliphatic $C_1$ to $C_8$ alcohols or glycerol, bis(sulpho-$C_2$- to $C_6$-alkyl) $C_3$- to $C_{12}$-alkanedicarboxylates, bis(sulpho-$C_2$- to $C_6$-alkyl) itaconates, (sulpho-$C_2$- to $C_6$-alkyl) $C_6$- to $C_{18}$-alkanecarboxylates, (sulpho-$C_2$- to $C_5$-alkyl) acrylates or methacrylates, triscatechol phosphate optionally substituted by up to 12 halogen radicals, an anion from the group of tetraphenylborate, cyanotriphenylborate, tetraphenoxyborate, $C_4$- to $C_{12}$-alkyltriphenylborate, wherein the phenyl or phenoxy radicals may be substituted by halogen, $C_1$- to $C_4$-alkyl and/or $C_1$- to $C_4$-alkoxy, $C_4$- to $C_{12}$-alkyltrinaphthylborate, tetra-$C_1$- to $C_{20}$-alkoxyborate, 7,8- or 7,9-dicarba-nido-undecaborate(1-) or (2-), which are optionally substituted on the boron and/or carbon atoms by one or two $C_1$- to $C_{12}$-alkyl or phenyl groups, dodecahydrodicarbadodecaborate(2-) or B—$C_1$- to $C_{12}$-alkyl-C-phenyldodecahydrodicarbadodecaborate(1-), where, in the case of polyvalent anions such as naphthalenedisulphonate, $A^-$ represents one equivalent of this anion, and where the alkane and alkyl groups may be branched and/or may be substituted by halogen, cyano, methoxy, ethoxy, methoxycarbonyl or ethoxycarbonyl.

It is also preferable when the anion $A^-$ of the dye has an AC log P in the range from 1 to 30, more preferably in the range from 1 to 12 and especially preferably in the range from 1 to 6.5. AC log P is computed after J. Comput. Aid. Mol. Des. 2005, 19, 453; Virtual Computational Chemistry Laboratory, http://www.vcclab.org.

Suitable ammonium alkylarylborates are, for example (Cunningham et al., RadTech'98 North America UV/EB Conference Proceedings, Chicago, Apr. 19-22, 1998): tetrabutylammonium triphenylhexylborate, tetrabutylammonium triphenylbutylborate, tetrabutylammonium trinaphthylhexylborate, tetrabutylammonium tris(4-tert-butyl)phenylbutylborate, tetrabutylammonium tris(3-fluorophenyl)hexylborate hexylborate ([191726-69-9], CGI 7460, product from BASF SE, Basle, Switzerland), 1-methyl-3-octylimidazolium dipentyldiphenylborate and tetrabutylammonium tris (3-chloro-4-methylphenyl)hexylborate ([1147315-11-4], CCI 909, product from BASF SE, Basle, Switzerland).

It may be advantageous to use mixtures of these photoinitiators. According to the radiation source used, the type and concentration of photoinitiator has to be adjusted in the manner known to those skilled in the art. Further details are described, for example, in P. K. T. Oldring (Ed.), Chemistry & Technology of UV & EB Formulations For Coatings, Inks & Paints, Vol. 3, 1991, SITA Technology, London, p. 61-328.

It is most preferable when the photoinitiator comprises a combination of dyes whose absorption spectra at least partly cover the spectral range from 400 to 800 nm, with at least one coinitiator matched to the dyes.

It is also preferable when at least one photoinitiator suitable for a laser light colour selected from blue, green and red is present in the photopolymer formulation.

It is also further preferable when the photopolymer formulation contains one suitable photoinitiator each for at least two laser light colours selected from blue, green and red.

Finally, it is most preferable when the photopolymer formulation contains one suitable photoinitiator for each of the laser light colours blue, green and red.

In a further preferred embodiment, the photopolymer formulation additionally contains monomeric urethanes as additives, in which case the urethanes may especially be substituted by at least one fluorine atom.

Preferably, the urethanes may have the general formula (III)

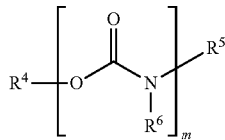

in which m≥1 and m≤8 and $R^4$, $R^5$ and $R^6$ are each a linear, branched, cyclic or heterocyclic organic moiety which is unsubstituted or else optionally substituted by heteroatoms and/or $R^5$, $R^6$ are each independently hydrogen, in which case preferably at least one of the $R^4$, $R^5$, $R^6$ moieties is substituted by at least one fluorine atom and, more preferably, $R^4$ is an organic radical having at least one fluorine atom. More preferably, $R^5$ is a linear, branched, cyclic or heterocyclic organic moiety which is unsubstituted or else optionally substituted by heteroatoms, for example fluorine.

The invention likewise provides a holographic medium comprising matrix polymers, writing monomers and photoinitiators, wherein the writing monomers comprise a compound of formula (I) according to the invention.

The further preferred embodiments described above for the photopolymer formulation of the invention also constitute preferred embodiments of the holographic medium according to the invention.

A preferred embodiment of the holographic medium provides that the matrix polymers are crosslinked matrix polymers, preferably three-dimensionally crosslinked matrix polymers and most preferably are three-dimensionally crosslinked polyurethanes.

It is also preferable for the holographic medium to comprise at least a fluorourethane as additive.

The holographic medium may be in particular a film, preferably with a film thickness of 0.5 μm to 200 μm, more preferably with a film thickness of 0.8 μm to 50 μm and yet more preferably with a film thickness of 1 μm to 25 μm.

The holographic medium may also contain at least one exposed hologram.

The inventive holographic media can be processed into holograms by means of appropriate exposure processes for optical applications over the entire visible and in the near UV range (300-800 nm). Visual holograms include all holograms which can be recorded by methods known to those skilled in the art. These include in-line (Gabor) holograms, off-axis holograms, full-aperture transfer holograms, white light transmission holograms ("rainbow holograms"), Denisyuk holograms, off-axis reflection holograms, edge-lit holograms and holographic stereograms. Preference is given to reflection holograms, Denisyuk holograms, transmission holograms.

Possible optical functions of the holograms correspond to the optical functions of light elements such as lenses, mirrors, deflecting mirrors, filters, diffuser lenses, directed diffusion elements, diffraction elements, light guides, waveguides, projection lenses and/or masks. It is likewise possible for combinations of these optical functions to be combined in one hologram independently of each other. These optical elements frequently have a frequency selectivity according to how the holograms have been exposed and the dimensions of the hologram.

In addition, by means of the inventive media, it is also possible to produce holographic images or representations, for example for personal portraits, biometric representations in security documents, or generally of images or image structures for advertising, security labels, brand protection, branding, labels, design elements, decorations, illustrations, collectable cards, images and the like, and also images which can represent digital data, including in combination with the products detailed above. Holographic images can have the impression of a three-dimensional image, but they may also represent image sequences, short films or a number of different objects according to the angle from which and the light source with which (including moving light sources) etc. they are illuminated. Because of this variety of possible designs, holograms, especially volume holograms, constitute an attractive technical solution for the abovementioned application.

The present invention accordingly further provides for the use of an inventive holographic medium for recording of in-line, off-axis, full-aperture transfer, white light transmission, Denisyuk, off-axis reflection or edge-lit holograms and also of holographic stereograms, in particular for production of optical elements, images or image depictions.

The present invention likewise provides a process for producing a holographic medium by using a photopolymer formulation of the present invention.

The photopolymer formulations can especially be used for production of holographic media in the form of a film. In this case, a ply of a material or material composite transparent to light within the visible spectral range (transmission greater than 85% within the wavelength range from 400 to 780 nm) as carrier substrate is coated on one or both sides, and a cover layer is optionally applied to the photopolymer ply or plies.

Preferred materials or material composites for the carrier substrate are based on polycarbonate (PC), polyethylene terephthalate (PET), polybutylene terephthalate, polyethylene, polypropylene, cellulose acetate, cellulose hydrate, cellulose nitrate, cycloolefin polymers, polystyrene, polyepoxides, polysulphone, cellulose triacetate (CTA), polyimide, polyinethylmethaerylate, polyvinyl chloride, polyvinyl butyral or polydicyclopentadiene or mixtures thereof. They are more preferably based on PC, PET and CTA. Material composites may be film laminates or coextrudates. Preferred material composites are duplex and triplex films formed according to one of the schemes A/B, A/B/A or A/B/C. Particular preference is given to PC/PET, PET/PC/PET and PC/TPU (TPU=thermoplastic polyurethane).

The materials or material composites of the carrier substrate may be given an antiadhesive, antistatic, hydrophobized or hydrophilized finish on one or both sides. The modifications mentioned serve the purpose, on the side facing the photopolymer layer, of making the photopolymer ply detachable without destruction from the carrier substrate. Modification of the opposite side of the carrier substrate from the photopolymer ply serves to ensure that the inventive media satisfy specific mechanical demands which exist, for example, in the case of processing in roll laminators, especially in roll-to-roll processes.

The invention additionally provides a display comprising an inventive holographic medium.

Examples of such displays are described for example in US 2009/174919 A1, WO 2012/035058 and in the unpublished application EP 14155599.5.

BRIEF DESCRIPTION OF THE FIGURES

FIG. 3 shows the schematic set-up for the coating system.

The invention will now be more particularly described by means of examples.

Methods of Measurement:

OH number: Reported OH numbers were determined to DIN 53240-2.

NCO value: Reported NCO values (is canate contents) were quantified to DIN EN ISO 11909.

Solids content: Reported solids content were determined to DIN EN ISO 3251.

Measurement of the Holographic Properties DE and Δn of the Holographic Media By Means of Twin Beam Interface in Reflection Arrangement The media obtained as described in "Preparation of media for determination of holographic properties" were tested for their holographic properties as follows using a measuring arrangement according to FIG. 1: The beam of a He—Ne laser (emission wavelength 633 nm) was converted to a parallel homogeneous beam with the aid of the spatial filter (SF) and together with the collimation lens (CL). The final cross sections of the signal and reference beam are fixed by the iris diaphragms (I). The diameter of the iris diaphragm opening is 0.4 cm. The polarization-dependent beam splitters (PBS) split the laser beam into two coherent beams of identical polarization. By means of the λ/2 plates, the power of the reference beam was set to 0.5 mW and the power of the signal beam to 0.65 mW. The powers were determined using the semiconductor detectors (D) with the sample removed. The angle of incidence ($\alpha_0$) of the reference beam is −21.8°; the angle of incidence ($\eta_0$) of the signal beam is 41.8°. The angles are measured proceeding from the sample normal to the beam direction. According to FIG. 1, therefore, $\alpha_0$ has a negative sign and $\beta_0$ a positive sign. At the location of the sample (medium), the interference field of the two overlapping beams produced a pattern of light and dark strips perpendicular to the angle bisectors of the two beams incident on the sample (reflection hologram). The strip spacing $\Lambda$, also called grating period, in the medium is ~225 nm (the refractive index of the medium assumed to be ~1.504).

Figure 1:
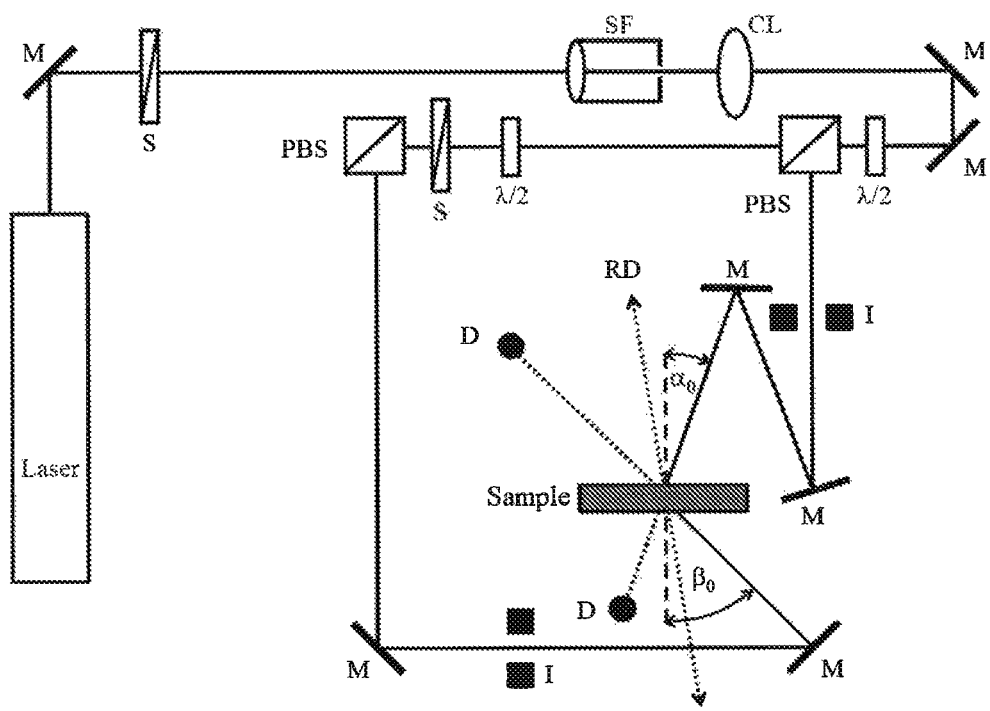
FIG. 1 shows the geometry of a holographic media tester.

FIG. 1 shows the geometry of a holographic media tester (HMT) at $\lambda$=633 nm (He—Ne laser): M=mirror, S=shutter, SF=spatial filter, CL=collimator lens, $\lambda/2=\lambda/2$ plate, PBS=polarization-sensitive beam splitter, D=detector, I=iris diaphragm, $\alpha_0$=−21.8°, $\beta_0$=41.8° are the angles of incidence of the coherent beams measured outside the sample (outside the medium). RD=reference direction of turntable. A holographic test setup as shown in FIG. 1 was used to measure the diffraction efficiency (DE) of the media.

Holograms were recorded in the medium in the following manner:
Both shutters (S) are opened for the exposure time t.
Thereafter, with the shutters (S) closed, the medium is allowed 5 minutes for the diffusion of the as yet unpolymerized writing monomers.

The written holograms were then read out in the following manner: The shutter of the signal beam remained closed. The shutter of the reference beam was opened. The iris diaphragm of the reference beam was closed to a diameter of ≤1 mm. This ensured that the beam was always completely within the previously recorded hologram for all angles of rotation ($\Omega$) of the medium. The turntable, under computer control, swept over the angle range from $\Omega_{min}$ to $\Omega_{max}$ with an angle step width of 0.05°. $\Omega$ is measured from the sample normal to the reference direction of the turntable. The reference direction of the turntable is obtained when the angles of incidence of the reference beam and of the signal beam have the same absolute value on recording of the hologram, i.e. $\alpha_0$=−31.8° and $\beta_0$=31.8°. In that case, $\Omega_{recording}$=0°. When $\alpha_0$=−21.8° and $\beta_0$=41.8°, $\Omega_{recording}$ is therefore 10°. In general, for the interference field in the course of recording of the hologram:

$$\alpha_0 = \theta_0 + \Omega_{recording}.$$

$\theta_0$ is the semiangle in the laboratory system outside the medium and, in the course of recording of the hologram:

$$\theta_0 = \frac{\alpha_0 - \beta_0}{2}.$$

Thus, in this case, $\theta_0$=−31.8°. At each setting for the angle of rotation $\Omega$, the powers of the beam transmitted in the zeroth order were measured by means of the corresponding detector D, and the powers of the beam diffracted in the first order by means of the detector D. The diffraction efficiency was calculated at each setting of angle $\Omega$ as the quotient of:

$$\eta = \frac{P_D}{P_D + P_T}$$

$P_D$ is the power in the detector for the diffracted beam and $P_T$ is the power in the detector for the transmitted beam.

By means of the process described above, the Bragg curve, which describes the diffraction efficiency $\eta$ as a function of the angle of rotation $\Omega$, for the recorded hologram, was measured and saved on a computer. In addition, the intensity transmitted into the zeroth order was also recorded against the angle of rotation $\Omega$ and saved on a computer.

The maximum diffraction efficiency (DE=$\eta_{max}$) of the hologram, i.e. the peak value thereof, was determined at $\Omega_{reconstruction}$. In some cases, it was necessary for this purpose to change the position of the detector for the diffracted beam in order to determine this maximum value.

The refractive index contrast $\Delta n$ and the thickness d of the photopolymer layer were now determined by means of coupled wave theory (see: H. Kogelnik, The Bell System Technical Journal, Volume 48, November 1969, Number 9 page 2909-page 2947) from the measured Bragg curve and the angle profile of the transmitted intensity. In this context, it should be noted that, because of the shrinkage in thickness which occurs as a result of the photopolymerization, the strip spacing $\Lambda'$ of the hologram and the orientation of the strips (slant) can differ from the strip spacing $\Lambda$ of the interference pattern and the orientation thereof. Accordingly, the angle $\alpha_0'$ and the corresponding angle of the turntable $\Omega_{reconstruction}$ at which maximum diffraction efficiency is achieved will also differ from $\alpha_0$ and from the corresponding $\Omega_{recording}$. This alters the Bragg condition. This alteration is taken into account in the evaluation process. The evaluation process is described hereinafter:

All geometric parameters which relate to the recorded hologram and not to the interference pattern are shown as parameters with primes.

For the Bragg curve $\eta(\Omega)$ of a reflection hologram, according to Kogelnik:

$$\eta = \begin{cases} \dfrac{1}{1 - \dfrac{1(\xi/\nu)^2}{\sin^2\left(\sqrt{\xi^2 - \nu^2}\right)}}, & \text{for } \nu^2 - \xi^2 < 0 \\ \dfrac{1}{1 + \dfrac{1 - (\xi/\nu)^2}{\sinh^2\left(\sqrt{\nu^2 - \xi^2}\right)}}, & \text{for } \nu^2 - \xi^2 \geq 0 \end{cases}$$

with:

$$\nu = \frac{\pi \cdot \Delta n \cdot d'}{\lambda \cdot \sqrt{|c_x \cdot c_r|}}$$

$$\xi = -\frac{d'}{2 \cdot c_s} \cdot DP$$

$$c_s = \cos(\vartheta') - \cos(\psi') \cdot \frac{\lambda}{n \cdot \Lambda'}$$

$$c_r = \cos(\vartheta')$$

$$DP = \frac{\pi}{\Lambda'} \cdot \left(2 \cdot \cos(\psi' - \vartheta') - \frac{\lambda}{n \cdot \Lambda'}\right)$$

$$\psi' = \frac{\beta' + \alpha'}{2}$$

$$\Lambda' = \frac{\lambda}{2 \cdot n \cdot \cos(\psi' - \alpha')}$$

The following holds for the reading out ("reconstruction") of the hologram similarly to the above explanation:

$$\vartheta'_0 = \theta_0 + \Omega$$

$$\sin(\vartheta'_0) = n \cdot \sin(\vartheta')$$

Under the Bragg condition, the "dephasing" DP=0. And it follows correspondingly that:

$$\alpha'_0 = \vartheta_0 + \Omega_{reconstruction}$$

$$\sin(\alpha'_0) = n \cdot \sin(\alpha')$$

The as yet unknown angle β' can be determined from the comparison of the Bragg condition of the interference field in the course of recording of the hologram and the Bragg condition in the course of reconstruction of the hologram, assuming that only shrinkage in thickness takes place. It then follows that:

$$\sin(\beta') = \frac{1}{n} \cdot [\sin(\alpha_0) + \sin(\beta_0) - \sin(\vartheta_0 + \Omega_{reconstruction})]$$

ν is the grating intensity, ξ is the detuning parameter and ψ' is the orientation (slant) of the refractive index grating written. α' and β' correspond to the angles $\alpha_0$ and $\beta_0$ of the interference field during the recording of the hologram, but measured in the medium and valid for the grating of the hologram (shrinkage in thickness). n is the average refractive index of the photopolymer and was set equal to 1.504. λ is the wavelength of the laser light in a vacuum.

The maximum diffraction efficiency (DE=$\eta_{max}$), when ξ=0, is then calculated to be:

$$DE = \tanh^2(v) = \tanh^2\left(\frac{\pi \cdot \Delta n \cdot d'}{\lambda \cdot \sqrt{\cos(\alpha') \cdot \cos(\alpha' - 2\psi)}}\right)$$

Figure 2:
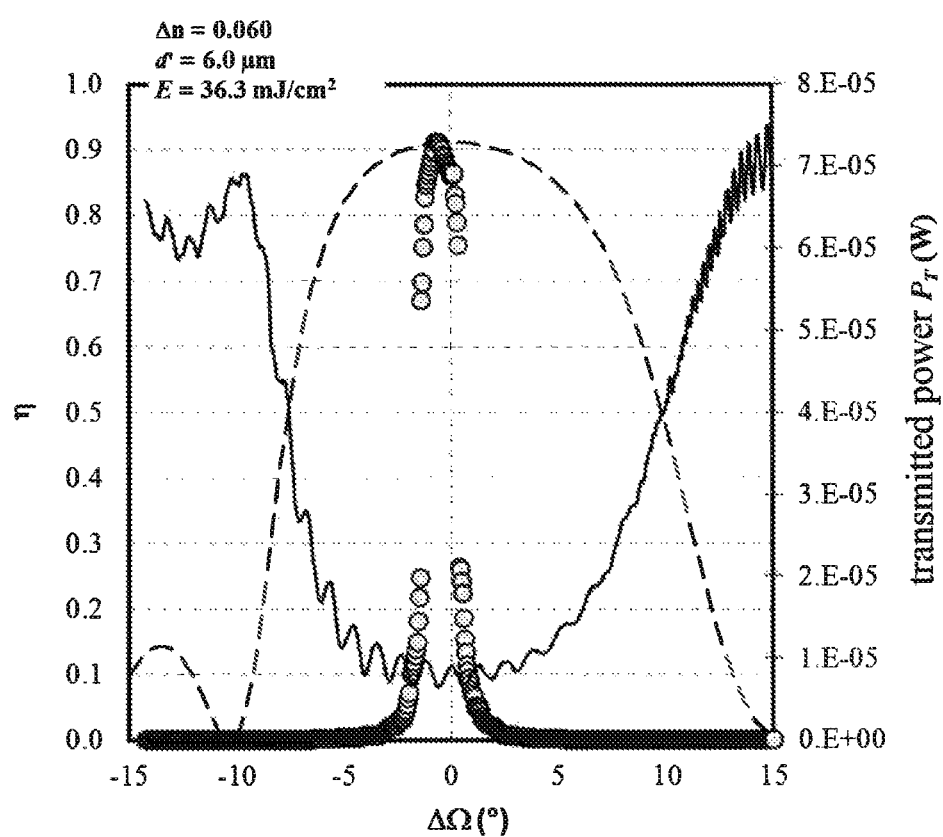
FIG. 2 shows the plot of the Bragg curve

FIG. 2 shows the measured transmitted power $P_T$ (right-hand y-axis) plotted as a solid line against the angle detuning ΔΩ; the measured diffraction efficiency η (left-hand y-axis) is plotted as filled circles against the angle detuning ΔΩ (to the extent allowed by the finite size of the detector), and the fitting to the Kogelnik theory as a broken line (left-hand y-axis).

The measured data for the diffraction efficiency, the theoretical Bragg curve and the transmitted intensity are, as shown in FIG. 2, plotted against the centred angle of rotation $\Delta\Omega = \Omega_{reconstruction} - \Omega = \alpha'_0 - \vartheta'_0$, also called angle detuning.

Since DE is known, the shape of the theoretical Bragg curve, according to Kogelnik, is determined only by the thickness d' of the photopolymer layer. Δn is corrected via DE for a given thickness d' such that measurement and theory for DE are always in agreement. d' is adjusted until the angle positions of the first secondary minima of the theoretical Bragg curve correspond to the angle positions of the first secondary maxima of the transmitted intensity, and there is additionally agreement in the full width at half maximum (FWHM) for the theoretical Bragg curve and for the transmitted intensity.

Since the direction in which a reflection hologram also rotates when reconstructed by means of an Ω scan, but the detector for the diffracted light can cover only a finite angle range, the Bragg curve of broad holograms (small d') is not fully covered in an Ω scan, but rather only the central region, given suitable detector positioning. Therefore, the shape of the transmitted intensity, which is complementary to the Bragg curve, is additionally employed for adjustment of the layer thickness d'.

FIG. 2 shows the plot of the Bragg curve η according to the coupled wave theory (broken line), the measured diffraction efficiency (filled circles) and the transmitted power (black solid line) against the angle detuning ΔΩ.

For a formulation, this procedure was repeated, possibly several times, for different exposure times t on different media, in order to find the mean energy dose of the incident laser beam in the course of recording of the hologram at which DE reaches the saturation value. The mean energy dose E is calculated as follows from the powers of the two component beams assigned to the angles $\alpha_0$ and $\beta_0$ (reference beam where $P_r$=0.50 mW and signal beam where $P_s$=0.63 mW), the exposure time t and the diameter of the iris diaphragm (0.4 cm):

$$E(mJ/cm^2) = \frac{2 \cdot [P_r + P_s] \cdot t(s)}{\pi \cdot 0.4^2 \; cm^2}$$

The powers of the component beams were adjusted such that the same power density is attained in the medium at the angles $\alpha_0$ and $\beta_0$ used.

Substances:

The solvents and reagents used were obtained commercially.

BINOL (+/+)-1,1'-bi(2-napthol) [602-09-5] is available from ABCR GmbH & Co. KG, Karlsruhe, Germany.

6,6'-Dibromo-1,1'-bi naphthalene-2,2'-diol [80655-81-8] is available from ABCR GmbH & Co. KG, Germany.

7-Methoxy-2-naphthol [5060-82-2] is available from Aldrich Chemie, Steinheim, Germany.

Methyl 3-hydroxy-2-naphthoate [883-99-8] is available from ABCR GmbH & Co. KG, Karlsruhe, Germany.

6-Bromo-2-naphthol [15231-91-1] is available from ABCR GmbH & Co. KG, Karlsruhe, Germany.

6-Cyano2-naphthol [52927-22-7] is available from ABCR GmbH & Co. KG, Karlsruhe, Germany.

2-(Phenylthio)-phenyl isocyanate [13739-55-4], is available from ABCR GmbH & Co. KG, Karlsruhe, Germany.

CGI-909 tetrabutylammonium tris(3-chloro-4-methylphenyl)(hexyl)borate [1147315-11-4] is a product manufactured by CIBA Inc., Basle, Switzerland.

Desmodur® N 3900 product from Bayer MaterialScience AG, Leverkusen, Del., hexane diisocyanate-based polyisocyanate, proportion of iminooxadiazinedione at least 30%, NCO content: 23.5%. 23.5%.

Desmodur® H product from Bayer MaterialScience AG, Leverkusen, Del., monomeric aliphatic diisocyanate, hexamethylene 1,6-diisocyanate (HDI) or 1,6-diisocyanatohexane, NCO content: ≤49.7%.

Vestanat TMDI product from Evonik Industries AG, Essen, Del., monomeric substituted aliphatic diisocyanate, an approximately 1:1 mixture of 2,2,4- and 2,4,4-trimethythexamethylene diisocyanate, This mixture is for reasons of clarity not reflected in the designation of the examples made in that only the particular 2,2,4-isomer was described. The 2,4,4-isomer, which is likewise formed, is likewise intended and encompassed.

Desmorapid Z dibutyltin dilaurate [77.58-7], product from. Bayer MaterialScience AG, Leverkusen, Germany.

Fomrez UL 28 urethanization catalyst, commercial product of Momentive Performance Chemicals, Wilton, Conn., USA.

Borchi® Kat 22 urethanization catalyst, product from OMG Borchers GmbH, Langenfeld, Germany.

KarenzAOI® 2-isocyanatoethyl acrylate, [13641-96-8], product from SHOWA DENKO K.K., Fine Chemicals Group, Specialty Chemicals Department, Chemicals Division.

KarenzMOI®2-isocyanatoethyl methacrylate, [30674-80-7], product from SHOWA DENKO K.K., Fine Chemicals Group, Specialty Chemicals Department, Chemicals Division.

Dye 1 C. I. Basic Blue 3 (as bis(2-ethylhexyl) sulphosuccinate) was prepared by the method known from WO2012062655, Example 9.

Unless otherwise indicated, percentages are all by weight.

Example 1: 2-[({[2'-({[2-(Acryloyloxy)ethyl]carbamoyl}oxy)-1,1'-binaphthyl-2-yl]oxy}carbonyl)amino]ethyl methacrylate A 100 mL round-bottom flask was initially charged with 18.4 g of BINOL, 0.08 g of Desmorapid Z and 0.03 g of 2,6-ditert-butyl-4-methylphenol in 25 mL of dichloromethane. Then, a 1:1 mixture of 10.0 g of KarenzMOI® and 9.1 g of KarenzAOI® was added dropwise and the mixture was stirred at room temperature until the isocyanate content had fallen to below 0.1%. The product was then freed of dichloromethane on a rotary evaporator. The product was obtained as a colourless solid.

Example 2: Dimethyl 2,2'-bis({[2-(methacryloyloxy)ethyl]carbamoyl}oxy)-1,1'-binaphthyl-3,3'-dicarboxylate A 25 mL round-bottom flask was initially charged with 3.0 g of dimethyl 2,2'-dihydroxy-1,1'-binaphthyl-3,3'-dicarboxylate ([47644-69-9], prepared as described in Tetrahedron Letters (1994), 35(43), 7983-4), 0.01 g of Borchi® Kat 22 and 0.01 g of 2,6-ditert-butyl-4-methylphenol in 10 mL of ethyl acetate. Then, 2.3 g of KarenzMOI® were added dropwise and the mixture was stirred at 80° C. until the isocyanate content had fallen to below 0.1%. The product was then freed of ethyl acetate on a rotary evaporator. The product was obtained as a colourless solid.

Example 3: 1,1'-Binaphthyl-2,2'-diylbis(oxycarbonyliminoethane-2,1-diyl) bisacrylate A 250 mL round-bottom flask was initially charged with 40.0 g of BINOL, 0.18 g of Desmorapid Z and 0.06 g of 2,6-ditert-butyl-4-methylphenol in 80 mL of dichloromethane. Then, 39.4 g of KarenzAOI® were added dropwise and the mixture was stirred at room temperature until the isocyanate content had fallen to below 0.1%. The product was then freed of dichloromethane on a rotary evaporator. The product was obtained as a colourless solid.

Example 4: 1,1'-Binaphthyl-2,2'-diylbis(oxycarbonyliminoethane-2,1-diyl) bis(2-methylacrylate)

A 100 mL round-bottom flask was initially charged with 12.0 g of BINOL, 0.05 g of Desmorapid Z and 0.02 g of 2,6-ditert-butyl-4-methylphenol in 25 mL of dichloromethane. Then, 13.0 g of KarenzMOI® was added dropwise and the mixture was stirred at room temperature until the isocyanate content had fallen to below 0.1%. The product was then freed of dichloromethane on a rotary evaporator The product was obtained as a colourless solid.

Example 5: (6,6'-Dicyano-1,1'-binaphthyl-2,2'-diyl) bis(oxycarbonyliminoethane-2,1-diyl) bisacrylate A 25 mL round-bottom flask was initially charged with 3.0 g of 2,2'-dihydroxy-1,1'-binaphthyl-6,6'-dicarbonitrile ([164171-19-1], prepared from 6-cyano-2-naphthol as described in Tetrahedron Letters (1994), 35(43), 7983-4), 0.01 g of Borchi® Kat 22 and 0.01 g of 2,6-ditert-butyl-4-methylphenol in 10 mL of ethyl acetate. Then, 2.5 g of KarenzAOI® were added dropwise and the mixture was stirred at 80° C. until the isocyanate content had fallen to below 0.1%. The product was then freed of ethyl acetate on a rotary evaporator. The product was obtained as a colourless solid.

Example 6: (6,6'-Dibroma-1,1'-binaphthyl-2,2'-diyl) bis(oxycarbonyliminoethane-2,1-diyl) bisacrylate A 25 mL round-bottom flask was initially charged with 2.5 g of 6,6'-dibromo-1,1'-binaphthyl-2,2'-diol ([80655-81-8], available from ABCR GmbH & Co. KG, Karlsruhe, Germany), 0.01 g of Borchi® Kat 22 and 0.01 g of 2,6-ditert-butyl-4-methylphenol in 10 mL of ethyl acetate. Then, 1.6 g of KarenzAOI® were added dropwise and the mixture was stirred at 80° C. until the isocyanate content had fallen to below 0.1%. The product was then freed of ethyl acetate on a rotary evaporator. The product was obtained as a colourless solid.

Example 7: (6,6'-Dibromo-1,1'-binaphthyl-2,2'-diyl) bis(oxycarbonyliminoetbane-2,1-diyl) bis(2-methylacrylate)

A 25 mL round-bottom flask was initially charged with 2.5 g of 6,6'-dibromo-1,1'-binaphthyl-2,2'-diol ([80655-81-8], available from ABCR GmbH & Co. KG, Karlsruhe, Germany), 0.01 g of Borchi® Kat 22 and 0.01 g of 2,6-ditert-butyl-4-methylphenol in 10 mL of ethyl acetate. Then, 1.7 g of KarenzMOI® were added dropwise and the mixture was stirred at 80° C. until the isocyanate content had fallen to below 0.1% The product was then freed of ethyl acetate on a rotary evaporator. The product was obtained as a colourless solid.

Example 8: (7,7'-Dimethoxy-1,1'-binaphthyl-2,2'-diyl)bis(oxycarbonyliminoethane-2,1-diyl) bisacrylate A 25 mL round-bottom flask was initially charged with 3.0 g of 7,7'-dimethoxy-1,1'-binaphthyl-2,2'-diol ([128702-28-3], prepared from 7-methoxy-2-naphthol as described in Tetrahedron Letters (1994), 35(43). 7983-4), 0.01 g of Borchi® Kat 22 and 0.01 g of 2,6-ditert-butyl-4-methylphenol in 10 mL of ethyl acetate. Then, 2.5 g of KarenzAOI® were added dropwise and the mixture was stirred at 80° C. until the isocyanate content had fallen to below 0.1%. The product was then freed of ethyl acetate on a rotary evaporator. The product was obtained as a colourless solid.

Example 9: 2-{[({2'-[(Hexylcarbamoyl)oxy]-1,1'-binaphthyl-2-yl}oxy)carbonyl]amino}ethyl acrylate A 250 mL round-bottom flask was initially charged with 34.6 g of BINOL and 0.09 g of Borchi® Kat 22 in 50 mL of ethyl acetate. Then, 15.4 g of hexyl isocyanate were added dropwise and the mixture was stirred at 80° C. until the isocyanate content had fallen to below 0.1%. The product was then freed of the ethyl acetate on a rotary evaporator. This gave 49.3 g of 2'-hydroxy-1,1'-binaphthyl-2-yl hexylcarbamate as a colourless solid.

A 100 mL round-bottom flask was initially charged with 18.6 g of 2'-hydroxy-1,1'-binaphthyl-2-yl hexylcarbamate, 0.03 g of Borchi® Kat 22 and 0.01 g of 2,6-ditert-butyl-4-methylphenol in 25 mL of ethyl acetate. Then, 6.35 g of KarenzAOI® were added dropwise and the mixture was stirred at 80° C. until the isocyanate content had fallen to below 0.1%. The product was then freed of the ethyl acetate on a rotary evaporator. The product was obtained as a colourless solid.

Example 10: 2-{[({2-[(Hexylcarbamayl)oxy]-1,1'-binaphthyl-2-yl}oxy)carbonyl]amino}ethyl methacrylate A 100 mL round-bottom flask was initially charged with 18.1 g of 2'-hydroxy-1,1'-binaphthyl-2-yl hexylcarbamate (see Example 9), 0.03 g of Borchi® Kat 22 and 0.01 g of 2,6-ditert-butyl-4-methylphenol in 25 mL of ethyl acetate. Then, 6.81 g of KarenzMOI® were added dropwise and the mixture was stirred at 80° C. until the isocyanate content had fallen to below 0.1%. The product was then freed of the ethyl acetate on a rotary evaporator. The product was obtained as a colourless solid.

Example 11: 2-{[({2'-[(Hexylcarbamoyl)oxy]-1,1'-bhiaphthyl-2-yl}oxy)carbonyl]amino}ethyl acrylate A 250 mL round-bottom flask was initially charged with 35.3 g of BINOL and 0.09 g of Borchi® Kat 22 in 50 mL of ethyl acetate. Then, 14.7 g of phenyl isocyanate were added dropwise and the mixture was stirred at 80° C. until the isocyanate content had fallen to below 0.1%. The product was then freed of the ethyl acetate on a rotary evaporator. This gave 49.2 g of 2'-hydroxy-1,1'-binaphthyl-2-yl phenylcarbamate as a colourless solid.

A 100 mL round-bottom flask was initially charged with 18.5 g of 2'-hydroxy-1,1'-binaphthyl-2-yl phenylcarbamate, 0.03 g of Borchi® Kat 22 and 0.01 g of 2,6-ditert-butyl-4-methylphenol in 25 mL of ethyl acetate. Then, 6.44 g of KarenzAOI® were added dropwise and the mixture was stirred at 80° C. until the isocyanate content had fallen to below 0.1%. The product was then freed of the ethyl acetate on a rotary evaporator. The product was obtained as a colourless solid.

Example 12: 2-{[({2'-[(Hexylcarbamoyl)oxy]-1,1'-binaphthyl-2-yl}oxy)carbonyl]amino}ethyl acrylate A 100 mL round-bottom flask was initially charged with 18.0 g of 2'-hydroxy-1,1'-binaphthyl-2-ylphenylcarbamate (see Example 11), 0.03 g of Borchi® Kat 22 and 0.01 g of 2,6-ditert-butyl-4-methylphenol in 25 mL of ethyl acetate. Then, 6.90 g of KarenzMOI® were added dropwise and the mixture was stirred at 80° C. until the isocyanate content had fallen to below 0.1%. The product was then freed of the ethyl acetate on a rotary evaporator. The product was obtained as a colourless solid.

Example 13: 2-[({[2'-({[3-(Methylsulphanyl)phenyl]carbamayl}oxy)-1,1'-binaphthyl-2-yl]oxy}carbonyl)amino]ethyl acrylate A 250 mL round-bottom flask was initially charged with 31.7 g of BINOL and 0.08 g of Borchi® Kat 22 in 50 mL of ethyl acetate. Then, 18.3 g of 3-methylthiophenyl isocyanate were added dropwise and the mixture was stirred at 80° C. until the isocyanate content had fallen to below 0.1%. The product was then freed of the ethyl acetate on a rotary evaporator. This gave 49.5 g of T-hydroxy-1,1'-binaphthyl-2-yl [3-(methylsulphanyl)phenyl]carbamate as a colourless solid.

A 100 mL round-bottom flask was initially charged with 19.0 g of 2'-hydroxy-1,1'-binaphthyl-2-yl [3-(methylsulphanyl)phenyl]carbamate, 0.03 g of Borchi® Kat 22 and 0.02 g of 2,6-ditert-butyl-4-methylphenol in 25 mL, of ethyl acetate. Then, 5.94 g of KarenzAOI® were added dropwise and the mixture was stirred at 80° C. until the isocyanate content had fallen to below 0.1%. The product was then freed of the ethyl acetate on a rotary evaporator. The product was obtained as a colourless solid.

Example 14: 2-{[({2'-[(Hexylcarbamayl)oxy]-1,1'-binaphthyl-2-yl}oxy)carbonyl]amino}ethyl methacrylate A 100 mL round-bottom flask was initially charged with 18.6 g of 2'-hydroxy-1,1'-binaphthyl-2-yl [3-(methylsulphanyl)phenyl]carbamate (see Example 13), 0.03 g of Borchi® Kat 22 and 0.01 g of 2,6-ditert-butyl-4-methylphenol in 25 mL of ethyl acetate. Then, 6.38 g of KarenzMOI® were added dropwise and the mixture was stirred at 80° C. until the isocyanate content had fallen to below 0.1%. The product was then freed of the ethyl acetate on a rotary evaporator. The product was obtained as a colourless solid.

Example 15: 2-[({[2'-({[3-(Methylsulphanyl)phenyl]carbamoyl}oxy)-1,1'-binaphthyl-2-yl]oxy}carbonyl)amino]ethyl acrylate A 250 mL round-bottom flask was initially charged with 27.8 g of BINOL and 0.07 g of Borchi® Kat 22 in 50 mL of ethyl acetate. Then, 22.1 g of 2-isocyanatophenyl phenyl sulphide ([13739-55-4] were added dropwise and the mixture was stirred at 80° C. until the isocyanate content had fallen to below 0.1%. The product was then freed of the ethyl acetate on a rotary evaporator. This gave 48.9 g of 2'-hydroxy-1,1'-binaphthyl-2-yl [2-(phenylsulphanyl)phenyl]carbamate as a colourless solid.

A 100 mL round-bottom flask was initially charged with 19.6 g of 2'-hydroxy-1,1'-binaphthyl-2-yl [2-(phenylsulphanyl)phenyl]carbamate, 0.03 g of Borchi® Kat 22 and 0.02 g of 2,6-ditert-butyl-4-methylphenol in 25 mL of ethyl acetate. Then, 5.38 g of KarenzAOI® were added dropwise and the mixture was stirred at 80° C. until the isocyanate content had fallen to below 0.1%. The product was then freed of the ethyl acetate on a rotary evaporator. The product was obtained as a colourless solid.

Example 16: 2-{[({2'-[(Hexylcarbamoyl)oxy]-1,1'-binaphthyl-2-yl}oxy)carbonyl]amino}ethyl methacrylate A 100 mL round-bottom flask was initially charged with 19.2 g of 2'-hydroxy-1,1'-binaphthyl-2-yl [2-(phenylsulphanyl)phenyl]carbamate (see Example 15), 0.03 g of Borchi® Kat 22 and 0.01 g of 2,6-ditert-butyl-4-methylphenol in 25 mL of ethyl acetate. Then, 5.79 g of KarenzMOI® were added dropwise and the mixture was stirred at 80° C. until the isocyanate content had fallen to below 0.1%. The product was then freed of the ethyl acetate on a rotary evaporator. The product was obtained as a colourless solid.

Example 17: 2-{[({2'-[(1-Naphthylcarbamoyl)oxy]-1,1'-binaphthyl-2-yl}oxy)carbonyl]amino}ethyl acrylate A 250 mL round-bottom flask was initially charged with 31.4 g of BINOL and 0.08 g of Borchi® Kat 22 in 50 mL of ethyl acetate. Then, 18.5 g of 1-naphthyl isocyanate were added dropwise and the mixture was stirred at 80° C. until the isocyanate content had fallen to below 0.1%. The product was then freed of the ethyl acetate on a rotary evaporator. This gave 49.1 g of 2'-hydroxy-1,1'-binaphthyl-2-yl 1-naphthylcarbamate as a colourless solid.

A 100 mL round-bottom flask was initially charged with 19.0 g of 2'-hydroxy-1,1'-binaphthyl-2-yl [2-(phenylsulphanyl)phenyl]carbamate, 0.03 g of Borchi® Kat 22 and 0.02 g of 2,6-ditert-butyl-4-methylphenol in 25 of ethyl acetate. Then, 5.90 g of KarenzAOI® were added dropwise and the mixture was stirred at 80° C. until the isocyanate content fallen to below 0.1%. The product was then freed of the ethyl acetate on a rotary evaporator. The product was obtained as a colourless solid.

Example 18: 2-{[({2'-[(1-Naphthylcarbamoyl)oxy]-1,1'-binaphthyl-2-yl}oxy)carbonyl]amino}ethyl methacrylate A 100 mL round-bottom flask was initially charged with 18.6 g of 2'-hydroxy-1,1'-binaphthyl-2-yl 1-naphthylcarbamate (see Example 17), 0.03 g of Borchi® Kat 22 and 0.01 g of 2,6-ditert-butyl-4-methylphenol in 25 mL of ethyl acetate. Then, 6.34 g of KarenzMOI® were added dropwise and the mixture was stirred at 80° C. until the isocyanate content had fallen to below 0.1%. The product was then freed of the ethyl acetate on a rotary evaporator. The product was obtained as a colourless solid.

Example 19: Hexane-1,6-diylbis(carbamoyloxy-1, 1'-binaphthyle-2',2-diyloxycarbonyliminoethane-2,1-diyl) bisacrylate A 250 mL round-bottom flask was charged initially with 37.2 g of BINOL in 150 g of ethyl acetate at 80° C. and then with 0.005 g of Desmorapid Z. A 10.7 g quantity of hexamethylene diisocyanate (Desmodur H, product from Bayer MaterialScience AG, NCO content >49.7%) was admixed under intensive stirring, the stirring being continued at this temperature until the isocyanate content had dropped to below 0.1%. The bis(2'-hydroxy-1,1'-binaphthyl-2-yl) hexane-1,6-diylbiscarbamate thus obtained had a solids content of 24.2% in ethyl acetate.

A 61.2 g quantity of the above solution of bis(2¹-hydroxy-1,1'-binaphthyl-2-yl) hexane-1,6-diylbiscarbamate in ethyl acetate was admixed with 5.6 g of KarenzAOI® added dropwise at 80° C. under an air stream, and stirred at this temperature until the isocyanate content had dropped to below 0.1%. The product was then freed of the ethyl acetate on a rotary evaporator. The product was obtained as a colourless oil.

Example 20: Hexane-1,6-diylbis(carbamoylaxy-1,1'-binaphthyle-2',2-diyloxycarbonyliminoethane-2,1-diyl) bis(2-methylacrylate)

A 61.2 g quantity of the solution of bis(2)-hydroxy-1,1'-binaphthyl-2-yl) hexane-1,6-diylbiscarbamate (see Example 19) in ethyl acetate was admixed with 6.2 g of KarenzMOI® added dropwise at 80° C. under an air stream, and stirred at this temperature until the isocyanate content had dropped to below 0.1%. The product was then freed of the ethyl acetate on a rotary evaporator. The product was obtained as a colourless oil.

Example 21.1: (2,2,4-Trimethylhexane-1,6-diyl)bis (carbamoyloxy-1,1'-binaphthyl-2',2-diyloxycarbonyliminoethane-2,1-diyl) bisacrylate A 250 mL round-bottom flask was charged initially with 40.1 g of BINOL in 150 g of ethyl acetate at 80° C. and then with 0.005 g of Desmorapid Z. A 14.5 g quantity of trimethylhexamethylene diisocyanate (Vestanat TMDI, product from Evonik Industries, NCO content=40.0%) was admixed under intensive stirring, the stirring being continued at this temperature until the isocyanate content had dropped to below 0.1%. The bis(2'-hydroxy-1,1'-binaphthyl-2-yl) (2,2,4-trimethylhexane-1,6-diyl)biscarbamate thus obtained had a solids content of 26.7% in ethyl acetate.

A 58.7 g quantity of the above solution of bis(2'-hydroxy-1,1'-binaphthyl-2-yl) (2,2,4-trimethylhexane-1,6-diyl)biscarbamate in ethyl acetate was admixed with 5.6 g of Karen-zAOI® added dropwise at 80° C. under an air stream, and stirred at this temperature until the isocyanate content had dropped to below 0.1%. The product was then freed of the ethyl acetate on a rotary evaporator. The product was obtained as a colourless oil.

Example 22: (2,2,4-Trimethylhexane-1,6-diyl)bis (carbamoyloxy-1,1'-binaphthyl-2',2-diyloxycarbonyliminoethane-2,1-diyl) bis(2-methylacrylate)

A 58.7 g quantity of the solution of bis(2'-hydroxy-1,1'-binaphthyl-2-yl) (2,2,4-trimethylhexane-1,6-diyl)biscarbamate in ethyl acetate (see Example 21) was admixed with 6.2 g of KarenzMOI® added dropwise at 80° C. under an air stream, and stirred at this temperature until the isocyanate content had dropped to below 0.1%. The product was then freed of the ethyl acetate on a rotary evaporator. The product was obtained as a colourless oil.

Example 23: 2-({[(2'-{[(3-{[({[2'-({[2-(Acryloyloxy)ethyl]carbamoyl}oxy)-1,1'-binaphthyl-2-yl]oxy}carbonyl)amino]methyl}-3,5,5-trimethyleyclahexyl)carbamoyl]-oxy}-1,1'-binaphthyl-2-yl)oxy]carbonyl}amino)ethyl acrylate A 250 mL round-bottom flask was charged initially with 40.1 g of BINOL in 150 g of ethyl acetate at 80° C. and then with 0.005 g of Desmorapid Z. A 15.2 g quantity of 3-isocyanatomethyl-3,5,5-trimethylcyclohexyl isocyanat (Desmodur I, isophorone diisocyanat (IPDI), product from Bayer MaterialScience AG, NCO content >37.5%) was admixed under intensive stirring, the stirring being continued at this temperature until the isocyanate content had dropped to below 0.1%. The T-hydroxy-1,1'-binaphthyl-2-yl{3-[({[(2'-hydroxy-1,1'-binaphthyl-2-yl)oxy]carbonyl}amino)methyl]3,5,5-trimethylcyclohexyl}carbamate thus obtained had a solids content of 26.9% in ethyl acetate.

A 59.1 g quantity of the above solution of 2'-hydroxy-1, 1'-binaphthyl-2-yl{3-[({[(2'-hydroxy-1,1'-binaphthyl-2-yl)oxy]carbonyl}amino)methyl]3,5,5-trimethylcyclohexyl}carbamate in ethyl acetate was admixed with 5.6 g of KarenzAOI® added dropwise at 80° C. under an air stream, and stirred at this temperature until the isocyanate content had dropped to below 0.1%. The product was then freed of the ethyl acetate on a rotary evaporator. The product was obtained as a colourless oil.

Example 24: 2-({[(2'-{[(3-{[({[2'-({[2-(Methacryloyloxy)ethyl]carbamoyl}oxy)-1,1'-binaphthyl-2-yl]oxy}carbonyl)amino]methyl}-3,5,5-trimethylcyclohexyl)carbamoyl]oxy}-1,1'-binaphthyl-2-yl)oxy]carbonyl}amino)ethyl methacrylate)

A 59.1 g quantity of the solution of 2'-hydroxy-1,1'-binaphthyl-2-yl {3-[({[(2'-hydroxy-1,1'-binaphthyl-2-yl)oxy]carbonyl}amino)methyl]3,5,5-trimethylcyclohexyl} carbamate in ethyl acetate (see Example 23) was admixed with 6.2 g of KarenzMOI® added dropwise at 80° C. under an air stream, and stirred at this temperature until the isocyanate content had dropped to below 0.1%. The product was then freed of the ethyl acetate on a rotary evaporator. The product was obtained as a colourless oil.

Example 25: (6-Bromo-1,1'-binaphthyl-2,2'-diyl)bis(oxycarbonyliminoethane-2,1-diyl) bisacrylate In a glass beaker, 16.0 g of 2-naphtol, 22.5 g of 6-bromo-2-naphthol and 1.5 g of CuCl(OH)*TMEDA (prepared as described in Tetrahedron Letters 1994 (35), 7983-7984) were intensively mixed and then heated to 100° C. for 120 min. The mixture obtained was washed with 200 mL of 10% ammonia solution and twice with 200 mL of water, dried and purified by chromatography. This gave 21.2 g of 6-bromo-1,1'-binaphthyl-2,2'-diol.

4.41 g of 6-bromo-1,1'-binaphthyl-2,2'-diol were added together with 0.015 g of Desmorapid Z and 0.01 g of 2,6-ditert-butyl-4-methylphenol to the initial charge of 25 mL ethyl acetate. Then, 3.41 g of KarenzAOI® were added dropwise and the mixture was stirred at 80° C. until the isocyanate content had dropped to below 0.1%. The product was then freed of the ethyl acetate on a rotary evaporator. The product was obtained as a colourless solid.

Example 26: (6-Bromo-1,1'-binaphthyl-2,2'-diyl)bis(oxycarbonyliminoethane-2,1-diyl) bis(2-methylacrylate)

4.23 g of 6-bromo-1,1'-binaphthyl-2,2'-diol (prepared as described in Example 25) were added together with 0.015 g of Desmorapid Z and 0.01 g of 2,6-ditert-butyl-4-methylphenol to the initial charge of 25 mL ethyl acetate. Then, 3.59 g of KarenzMOI® were added dropwise and the mixture was stirred at 80° C. until the isocyanate content had dropped to below 0.1%. The product was then freed of the ethyl acetate on a rotary evaporator. The product was obtained as a colourless solid.

Example 27: (6-Cyano-1,1'-binaphthyl-2,2'-diyl)bis(oxycarbonyliminoethane-2,1-diyl) bisacrylate In a glass beaker, 20.8 g of 2-naphtol, 22.2 g of 6-cyano-2-naphthol and 1.5 g of CuCl(OH)*TMEDA (prepared as described in Tetrahedron Letters 1994 (35), 7983-7984) were intensively mixed and then heated to 100° C. for 120 min. The mixture obtained was washed with 200 mL of 10% ammonia solution and twice with 200 mL of water, dried and purified by chromatography. This gave 4.80 g of 6-cyano-1,1'-binaphthyl-2,2'-diol.

4.10 g of 6-cyano-1,1'-binaphthyl-2,2'-diol were added together with 0.015 g of Desmorapid Z and 0.01 g of 2,6-ditert-butyl-4-methylphenol to the initial charge of 25 mL ethyl acetate. Then, 3.72 g of KarenzAOI® were added dropwise and the mixture was stirred at 80° C. until the isocyanate content had dropped to below 0.1%. The product was then freed of the ethyl acetate on a rotary evaporator. The product was obtained as a colourless solid.

Example 28: (6-Cyano-1,1'-binaphthyl-2,2'-diyl)bis(oxycarbonyliminoethane-2,1-diyl) bis(2-methylacrylate)

3.92 g of 6-cyano-1,1'-binaphthyl-2,2'-diol (prepared as described in Example 27) were added together with 0.015 g of Desmorapid Z and 0.01 g of 2,6-ditert-butyl-4-methylphenol to the initial charge of 25 mL ethyl acetate. Then, 3.90 g of KarenzMOI® were added dropwise and the mixture was stirred at 80° C. until the isocyanate content had dropped to below 0.1%. The product was then freed of the ethyl acetate on a rotary evaporator. The product was obtained as a colourless solid.

Example 29: (6-Bromo-6'-cyano-1,1'-binaphthyl-2,2'-diyl)bis(oxycarbonyliminoethane-2,1-diyl) bisacrylate In a glass beaker, 22.8 g of 6-bromo-2-naphtol, 15.8 g of 6-cyano-2-naphthol and 1.4 g of CuCl(OH)*TMEDA (prepared as described in Tetrahedron Letters 1994 (35), 7983-7984) were intensively mixed and then heated to 100° C. for 120 min. The mixture obtained was washed with 200 mL of 10% ammonia solution and twice with 200 mL of water, dried and purified by chromatography. This gave 4.70 g of 6'-bromo-2,2'-dihydroxy-1,1'-binaphthyl-6-carbonitrile.

4.54 g of 6'-bromo-2,2'-dihydroxy-1,1'-binaphthyl-6-carbonitrile were added together with 0.015 g of Desmorapid Z and 0.01 g of 2,6-ditert-butyl-4-methylphenol to the initial charge of 25 mL ethyl acetate. Then, 3.28 g of KarenzAOI® were added dropwise and the mixture was stirred at 80° C. until the isocyanate content had dropped to below 0.1%. The product was then freed of the ethyl acetate on a rotary evaporator. The product was obtained as a colourless solid.

Example 30: (6-Bromo-6'-cyano-1,1'-binaphthyl-2,2'-diyl)bis(oxycarbonyliminoethane-2,1-diyl) bis(2-methylacrylate)

4.36 g of 6'-bromo-2,2'-dihydroxy-1,1'-binaphthyl-6-carbonitrile (prepared as described in Example 29) were added together with 0.015 g of Desmorapid Z and 0.01 g of 2,6-ditert-butyl-4-methylphenol to the initial charge of 25 mL ethyl acetate. Then, 3.46 g of KarenzMOI® were added dropwise and the mixture was stirred at 80° C. until the isocyanate content had dropped to below 0.1%. The product was then freed of the ethyl acetate on a rotary evaporator. The product was obtained as a colourless solid.

Preparation of Further Components for the Photopolymer Formulation:

Preparation of Polyol 1:

A 1 l flask was initially charged with 0.18 g of tin octoate, 374.8 g of ε-caprolactone and 374.8 g of a difunctional polytetrahydrofuran polyether polyol (equivalent weight 500 g/mol OH), which were heated to 120° C. and kept at this temperature until the solids content (proportion of nonvolatile constituents) was 99.5% by weight or higher. Subsequently, the mixture was cooled and the product was obtained as a waxy solid.

Preparation of Urethane Acrylate (Writing Monomer) 1: 2-({[3-(Methylsulphanyl)phenyl]carbamoyl}oxy)ethyl prop-2-enoate A 100 ml round-bottom flask was initially charged with 0.02 g of 2,6-di-tert-butyl-4-methylphenol, 0.01 g of Desmorapid Z, 11.7 g of 3-(methylthio)phenyl isocyanate [28479-1-8], and the mixture was heated to 60° C. Subsequently, 8.2 g of 2-hydroxyethyl acrylate were added dropwise and the mixture was still kept at 60° C. until the isocyanate content had fallen below 0.1%. This was followed by cooling. The product was obtained as a colourless liquid.

Preparation of additive 1 bis(2,2,3,3,4,4,5,5,6,6,7,7-dodecafluoroheptyl)(2,2,4-trimethythexane-1,6-diyl) biscarbamate A 50 ml round-bottom flask was initially charged with 0.02 g of Desmorapid Z and 3.6 g of Vestanat TMDI, and the mixture was heated to 60° C. Subsequently, 11.9 g of 2,2,3,3,4,4,5,5,6,6,7,7-dodecafluoroheptan-1-ol were added dropwise and the mixture was still kept at 60° C. until the isocyanate content had fallen below 0.1%. This was followed by cooling. The product was obtained as a colourless oil.

Preparation of Comparative Example 1 (Writing Monomer)

Phosphorothioyltris(oxybenzene-4,1-diylcarbamoyloxyethane-2,1-diyl) trisacrylate A 500 mL round-bottom flask was initially charged with 0.1 g of 2,6-di-tert-butyl-4-methylphenol, 0.05 g of dibutyltin dilaurate and 213.07 g of a 27% solution of tris(p-isocyanatophenyl) thiophosphate in ethyl acetate (Desmodur® RFE, product from Bayer MaterialScience AG, Leverkusen, Germany), which were heated to 60° C. Subsequently, 42.37 g of 2-hydroxyethyl acrylate were added dropwise and the mixture was still kept at 60° C. until the isocyanate content had fallen below 0.1%. This was followed by cooling and complete removal of the ethyl acetate in vacuo. The product was obtained as a partly crystal-line solid.

Preparation of Comparative Example 2 (Writing Monomer)

(Mixture of (4-methylbenzene-1,3-diyl)bis[carbamoyloxy-3-(biphenyl-2-yloxy)propane-2,1-diyl]bisacrylate and (4-methylbenzene-1,3-diyl)bis[carbamoyloxy3-(biphenyl-2-yloxy)propane-1,2-diyl] bisacrylate and analogous isomers)

A three-neck flask fitted with reflux condenser and stirrer was initially charged with 430.2 g of Denacol EX 142 (Nagase-Chemtex, Japan), 129.7 g of acrylic acid, 1.18 g of tri-phenylphosphine and 0.006 g of 2,6-ditert-butyl-4-methylphenol. In addition, the system was temperature-regulated to 60° C. and a slow stream of air was passed through it. The reaction mixture is then stirred at 90° C. for 24 hours. This gave a clear liquid of OH number=157.8 mg KOH/g. 21.3 g of this intermediate and 5.2 g of a mixture of 2,4- and 2,6-toluidene diisocyanate (Desmodur T80, Bayer MaterialScience AG, Leverkusen, Germany) were initially charged to a three-neck flask fitted with reflux condenser and stirrer. In addition, the system was temperature-regulated to 60° C. and a slow stream of air was passed through it. Following initial exothermism, the product was stirred at 60° C. for 24 hours. This gave a clear, colourless, glassy product with NCO=0%.

Production of Media to Determine the Holographic Properties

Example Medium I 338 g of polyol component 1 were mixed with 2.00 g of Example 1 as per formula (I), 2.00 g of urethane acrylate 2, 1.50 g of additive 1, 0.10 g of CGI 909, 0.026 g of dye 1 and 0.35 g of N-ethylpyrrolidone at 60° C. to obtain a clear solution. This was followed by cooling to 30° C., admixture of 0.65 g of Desmodur® N3900 and renewed mixing. This was finally followed by admixture of 0.01 g of Fomrez UL 28 and renewed brief mixing. The liquid mass obtained was then poured onto a glass plate and covered thereon with a second glass plate. This test specimen was left at room temperature for 12 hours for curing.

Example media II-IX were prepared as described under Example medium I. As listed in table 1, Example 1 was replaced by the same weight fraction of the example adduced in the particular row.

Comparative Medium V-I 3.38 g of polyol component 1 were mixed with 2.00 g of Comparative Example 1, 2.00 g of urethane acrylate 1, 1.50 g of additive 1, 0.10 g of CGI 909, 0.010 g of dye 1 and 0.35 g of N-ethylpyrrolidone at 60° C. to obtain a clear solution. This was followed by cooling to 30° C., admixture of 0.65 g of Desmodur® N3900 and renewed mixing. This was finally followed by admixture of 0.01 g of Fomrez UL 28 and renewed brief mixing. The liquid mass obtained was then poured onto a glass plate and covered thereon with a second glass plate. This test specimen was left at room temperature for 12 hours for curing.

Comparative Medium V-II 3.38 g of polyol component 1 were mixed with 2.00 g of Comparative Example 2, 2.00 g of urethane acrylate 1, 1.50 g of additive 1, 0.10 g of CGI 909, 0.010 g of dye 1 and 0.35 g of N-ethylpyrrolidone at 60° C. to obtain a clear solution. This was followed by cooling to 30° C., admixture of 0.65 g of Desmodur® N3900 and renewed mixing. This was finally followed by admixture of 0.01 g of Fomrez UL 28 and renewed brief mixing. The liquid mass obtained was then poured onto a glass plate and covered thereon with a second glass plate. This test specimen was left at room temperature for 12 hours for curing.

Production of Holographic Media on a Film Coating System

To achieve the most accurate determination of the refractive index modulation $\Delta n$ in a holographically exposed photopolymer by the method described above, the diffraction efficiency is not fully saturated but close to 100%. The diffraction efficiency DE depends on the product of $\Delta n$ and the layer thickness d of the photopolymer. The very bright holograms obtained here, which have a very high refractive index contrast $\Delta n$, therefore require the preparation of test specimens having a very thin layer thickness d. To this end, a selected example (Example 3) was processed into a photopolymer in a continuous coating system.

FIG. 3 shows the schematic set-up for the coating system used, featuring the following component parts:

1a, b stock reservoir vessel
2a, b metering unit
3a, b vacuum degassing unit
4a, b filter
5 static mixer
6 coating unit 7 circulating air dryer
8 carrier substrate
9 covering layer To prepare the photopolymer formulation, 45.7 g of polyol 1 in a stirred vessel was incrementally admixed with 290.0 g of ethyl acetate, 20.0 g of Example 1, 60.0 g of urethane-acrylate 1, 60.0 g of additive 1, 0.10 g of Fomrez UL 28, 1.80 g of BYK® 310 and 0.52 g of dye 1 to obtain a clear solution. This mixture was imported into stock reservoir vessel 1a of the coating system. The second stock reservoir vessel 1b was filled with a separately prepared clear mixture of 3.0 g of CGI 909, 8.87 of Desmodur N 3900 and 2.22 g of butyl acetate. The two components were then each fed by the metering units 2a and 2b in a ratio of 16.3:1 (stock reservoir vessel 1a:1b) to the vacuum degassing units 3a and 3b for degassing. From here, they were then each passed through the filters 4a and 4b into the static mixer 5, in which the components were mixed to give the photopolymer formulation. The liquid material obtained was then sent in the dark to the coating unit 6.

The coating unit 6 in the present case was a slot die known to a person skilled in the art. Alternatively, however, a doctor blade system or a roller application system can also be employed. With the aid of the coating unit 6, the photopolymer formulation was applied at a processing temperature of 20° C. to a carrier substrate 8 in the form of a 36 µm-thick polyethylene terephthalate film, and dried in an air circulation dryer 7 at a crosslinking temperature of 80° C. for 5.8 minutes. This gave a medium in the form of a film, which was then provided with a 40 µm-thick polyethylene film as covering layer 9 and wound up.

The layer thickness achieved in the film was 6-8 µm.

Holographic Testing:

The media obtained as described were tested for their holographic properties by using a measuring arrangement as per FIG. 1 in the manner described above. The following measurements were obtained for Δn at a fixed dose of 36 mJ/cm$^2$:

TABLE 1

Holographic assessment of selective examples

| Example medium | Example as per formula (I) | Δn |
|---|---|---|
| I | 1 | 0.043 |
| II | 3 | 0.050 |
| III | 4 | 0.051 |
| IV | 6 | 0.050 |
| V | 7 | 0.040 |
| VI | 8 | 0.040 |
| VII | 19 | 0.038 |
| VIII | 20 | 0.037 |
| IX | 22 | 0.038 |
| X | 3 | 0.060 |

TABLE 2

Holographic assessment of selected comparative media

| Comparative medium | Δn |
|---|---|
| V-I | 0.035 |
| V-II | 0.035 |

The values found for Example media I to IX show that the inventive formula (I) compounds used in the photopolymer formulations are very useful in holographic media having a very high refractive index modulation Δn. Comparative media V-1 and V-2 are free from any compound of formula (I) according to the invention and have lower Δn values in holographic media. Example medium X shows that the employed compounds of formula (I) according to the invention have a very high refractive index modulation Δn.

The invention claimed is:

1. A photopolymer formulation comprising matrix polymers, writing monomers and photoinitiators, wherein the writing monomers comprise a compound according of formula (I)

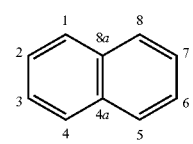

Formula (I)

a) which is substituted at least one of the carbon atoms 1, 2, 3, 4, 5, 6, 7, 8 with a moiety $R_{arcyl}$ of formula (II)

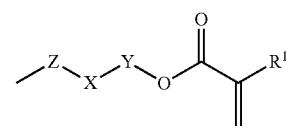

Formula (II)

where in said formula (II)
R$^1$ is hydrogen or a (C$_1$-C$_6$)-alkyl group,
X is a carboxamide (—C(O)N—) or a carboxylic ester (—C(O)O—) or a sulphonamide (—SO$_2$N—) group,
Y is a saturated or unsaturated or linear or branched optionally substituted moiety having 2-10 carbon atoms or a polyether having from one up to five (—CH$_2$—CH$_2$—O—)— or (—C(CH$_3$)H—CH$_2$—O—)— groups or a polyamine having from one to five nitrogen atoms, and
Z is oxygen or sulphur, b) and the compound of formula (I) is substituted at not less than one of carbon atoms 1, 2, 3, 4, 5, 6, 7, or 8 with a naphthalene moiety of formula (III)

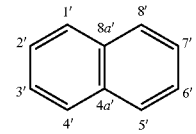

Formula (III)

where in said formula (III)
the carbon atoms of the compound of formula (III) are each independently substituted with hydrogen, halogen, a cyano group, a nitro group or an optionally substituted alkyl, alkenyl, alkynl, aralkyl, aryl or heteroaryl group or an optionally substituted alkoxy or alkylthio group or any substituted carbamoyl group, which also may be linked bridgingly to a moiety of formula (I), or a trifluoromethyl group or a trifluoromethoxy group or a moiety $R_{arcyl'}$ of formula (IV),

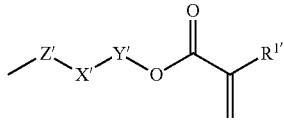

Formula (IV)

where in said formula (IV)
$R^{1'}$ is hydrogen or a (C1-C6)-alkyl group,
X' is a carboxamide (—C(O)N—) or a carboxylic ester (—C(O)O—) or a sulphonamide (—SO$_2$N—) group,
Y' is a saturated or unsaturated or linear or branched optionally substituted moiety having 2-10 carbon atoms or a polyether having from one to five (—CH$_2$—CH$_2$—O—)— or (—C(CH$_3$)H—CH$_2$—O—)— groups or a polyamine having from one to five nitrogen atoms, and
Z is oxygen or sulphur,
the remaining carbon atoms of the compound of formula (I) are each independently substituted with hydrogen, halogen, a cyano group, a nitro group or an optionally substituted alkyl, alkenyl, alkynyl, aralkyl, aryl or heteroaryl group or an optionally substituted alkoxy or alkylthio group or a trifluoromethyl group or a trifluoromethoxy group.

2. The photopolymer formulation according to claim 1, wherein it is substituted with the moiety of formula (III) on the carbon atom in position 5 of formula (I), wherein the moiety of formula (III) is preferably bonded to the carbon atom in position 5 via the carbon atom in position 8'.

3. The photopolymer formulation according to claim 1, wherein it is substituted with the moiety $R_{arcyl}$ of formula (II) on the carbon atom in position 6 of formula (I).

4. The photopolymer formulation according to claim 1, wherein the moiety of formula (III) is substituted with the moiety R' of formula (IV) on the carbon atom in position 7'.

5. The photopolymer formulation according to claim 1, wherein X is carboxamide in moiety $R_{arcyl}$ and/or X is carboxamide in moiety R'.

6. The photopolymer formulation according to claim 1, wherein $R_1$ is hydrogen or a $CH_3$ moiety in moiety $R_{arcyl}$ and/or $R_{1'}$ is hydrogen or a $CH_3$ moiety in moiety R'.

7. The photopolymer formulation according to claim 1, wherein Y is a —CH$_2$—CH$_2$— moiety in moiety $R_{arcyl}$ and/or Y' is a —CH$_2$—CH$_2$— moiety in moiety R'.

8. The photopolymer formulation according to claim 1, wherein Z and/or Z' are oxygen.

9. A holographic medium comprising the photopolymer formulation according to claim 1.

10. The holographic medium according to claim 9, wherein the matrix polymers are crosslinked matrix polymers.

11. The holographic medium according to claim 9, wherein the holographic medium comprises at least a fluorourethane as additive.

12. The holographic medium according to claim 9, wherein the holographic medium is a film.

13. The holographic medium according to claim 9, wherein the holographic medium contains at least one exposed hologram.

14. A display comprising a holographic medium according to claim 9.

15. The holographic medium according to claim 9, having a refractive index modulation Δn in the range from 0.037 to 0.060.

* * * * *